United States Patent [19]

Fujioka et al.

[11] Patent Number: 4,599,468

[45] Date of Patent: Jul. 8, 1986

[54] ETHER CARBOXALDEHYDES

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[21] Appl. No.: 744,569

[22] Filed: Jun. 14, 1985

Related U.S. Application Data

[60] Division of Ser. No. 673,105, Nov. 19, 1984, abandoned, which is a division of Ser. No. 533,915, Sep. 19, 1983, Pat. No. 4,532,364, which is a continuation-in-part of Ser. No. 507,292, Aug. 1, 1983, abandoned.

[51] Int. Cl.$^4$ ............... C07C 47/19; C07C 47/21; C07C 47/32; C07C 45/50
[52] U.S. Cl. ................... 568/420; 568/444; 568/446; 568/454; 568/496; 568/497
[58] Field of Search ............ 568/444, 446, 496, 497, 568/420, 454

[56] References Cited

U.S. PATENT DOCUMENTS 3,981,924  9/1976  Hall ........................... 568/446
4,205,186  5/1980  Sprecker et al. ............. 568/496 X
4,311,617  1/1982  Ansari et al. ............... 568/496 X
4,383,125  5/1983  Harris et al. ............... 568/496

FOREIGN PATENT DOCUMENTS 7200525  7/1973  Netherlands .................. 568/496

*Primary Examiner*—Bernard Helfin
*Attorney, Agent, or Firm*—Arthur L. Liberman

[57] ABSTRACT

Described are ether carboxaldehydes defined according to the generic structure:

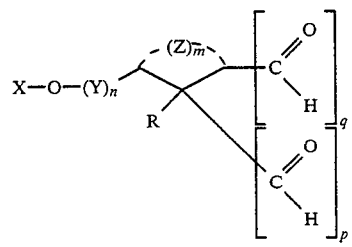

wherein X represents aryl, alkaryl, hydroxyalkyl, alkenyl, cycloalkenyl, lower alkyl or bicycloalkyl; wherein Y represents $C_1$-$C_3$ lower alkylene; wherein Z completes an alkyl substituted $C_6$ cycloalkyl ring or represents no moiety; wherein R represents hydrogen or methyl; wherein m represents 0 or 1; wherein n represents 0 or 1; wherein p represents 0 or 1 and wherein q represents 0 or 1 with the provisos that when m is 1, Z completes the alkyl substituted or unsubstituted $C_6$ cycloalkyl ring; that p is 1 when q is 0; and that when p is 0, q is 1, processes for producing same by reacting allyl ethers defined according to the structure:

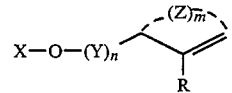

wherein x, y, z, m, n and r are as defined above with a mixture of carbon monoxide and hydrogen by means of an oxo reaction products produced according to said oxo reaction which are mixtures which contain the above-mentioned ether carboxaldehydes as well as methods for augmenting or enhancing the aroma or taste of consumable materials, including perfumes, colognes and perfumed articles; foodstuffs, chewing gums, chewing tobaccos, medicinal products and toothpastes; and smoking tobaccos and smoking tobacco articles by adding thereto aroma or taste augmenting or enhancing quantities of the thus produced ether carboxaldehydes or ether carboxaldehyde-containing mixtures.

Also described are perfume compositions, colognes, perfumed articles (including solid or liquid anionic, cationic, nonionic or zwitterionic detergents, fabric softener compositions, drier-added fabric softener articles, hair preparations, deodorant compositions, bleaching compositions and perfumed polymers), foodstuffs, chewing gums, toothpastes, medicinal products, chewing tobaccos, smoking tobaccos and smoking tobacco articles containing the products thus produced.

2 Claims, 24 Drawing Figures

FIG. 5 GLC PROFILE FOR BULKED FRACTIONS 2-4, 1st DISTILLATION.

FIG. 3 GLC PROFILE FOR FRACTION 4 OF EXAMPLE II.

NMR SPECTRUM FOR FRACTION 4 OF EXAMPLE II, PEAK "30" OF FIG. 3.

GLC PROFILE FOR EXAMPLE IV. CRUDE

GLC PROFILE FOR FRACTION 5 OF EXAMPLE III.

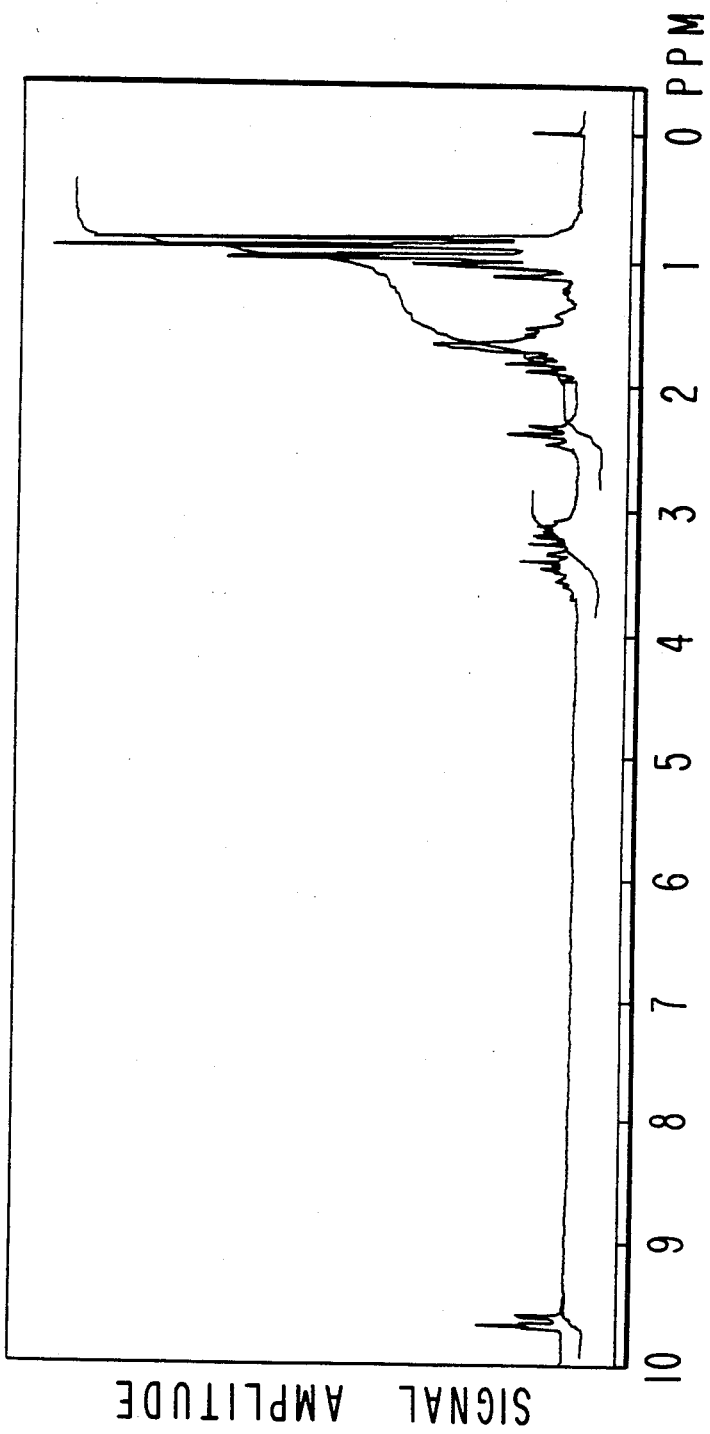

GLC PROFILE FOR FR.4 OF EXAMPLE V.
FIRST DISTILLATION

GLC PROFILE FOR FR.6 OF EXAMPLE IV.

NMR SPECTRUM FOR FRACTION 6 OF EXAMPLE IV.

GLC PROFILE FOR EXAMPLE VI.
CRUDE

GLC PROFILE FOR FRACTION 19 OF EXAMPLE V.
FINAL DISTILLATION

NMR SPECTRUM FOR FRACTION 19 OF EXAMPLE V.

GLC PROFILE FOR FRACTION 9 OF EXAMPLE VI.

GLC PROFILE FOR FRACTION 11 OF EXAMPLE VII.

NMR SPECTRUM FOR FRACTION 9 OF EXAMPLE VI

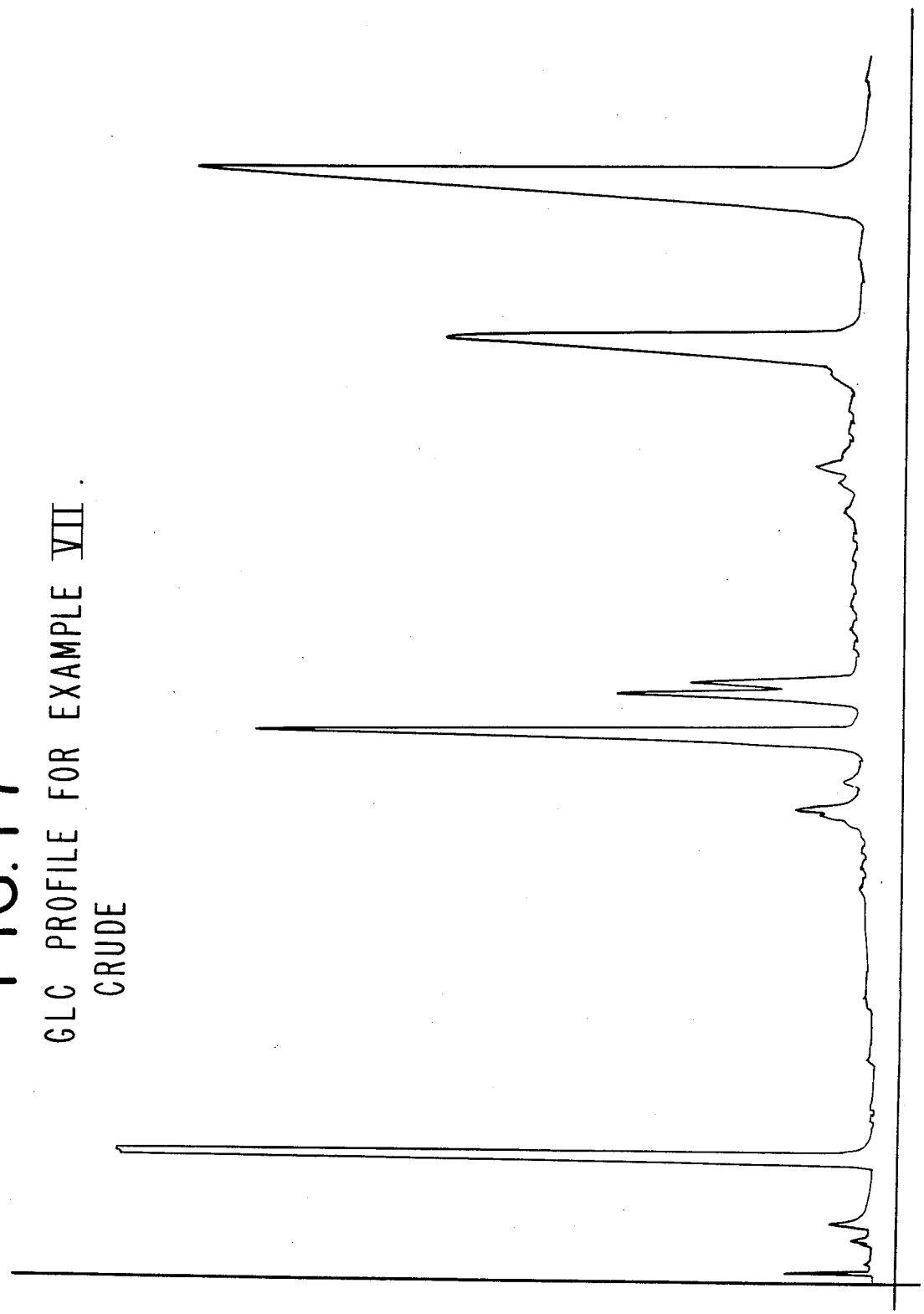
FIG. 17 GLC PROFILE FOR EXAMPLE VII. CRUDE

NMR SPECTRUM FOR FRACTION II OF EXAMPLE VII, PEAK 180 OF FIG.18.

GLC PROFILE FOR FRACTION 8 OF EXAMPLE VIII.

GLC PROFILE FOR EXAMPLE VIII. CRUDE

NMR SPECTRUM FOR EXAMPLE VIII.

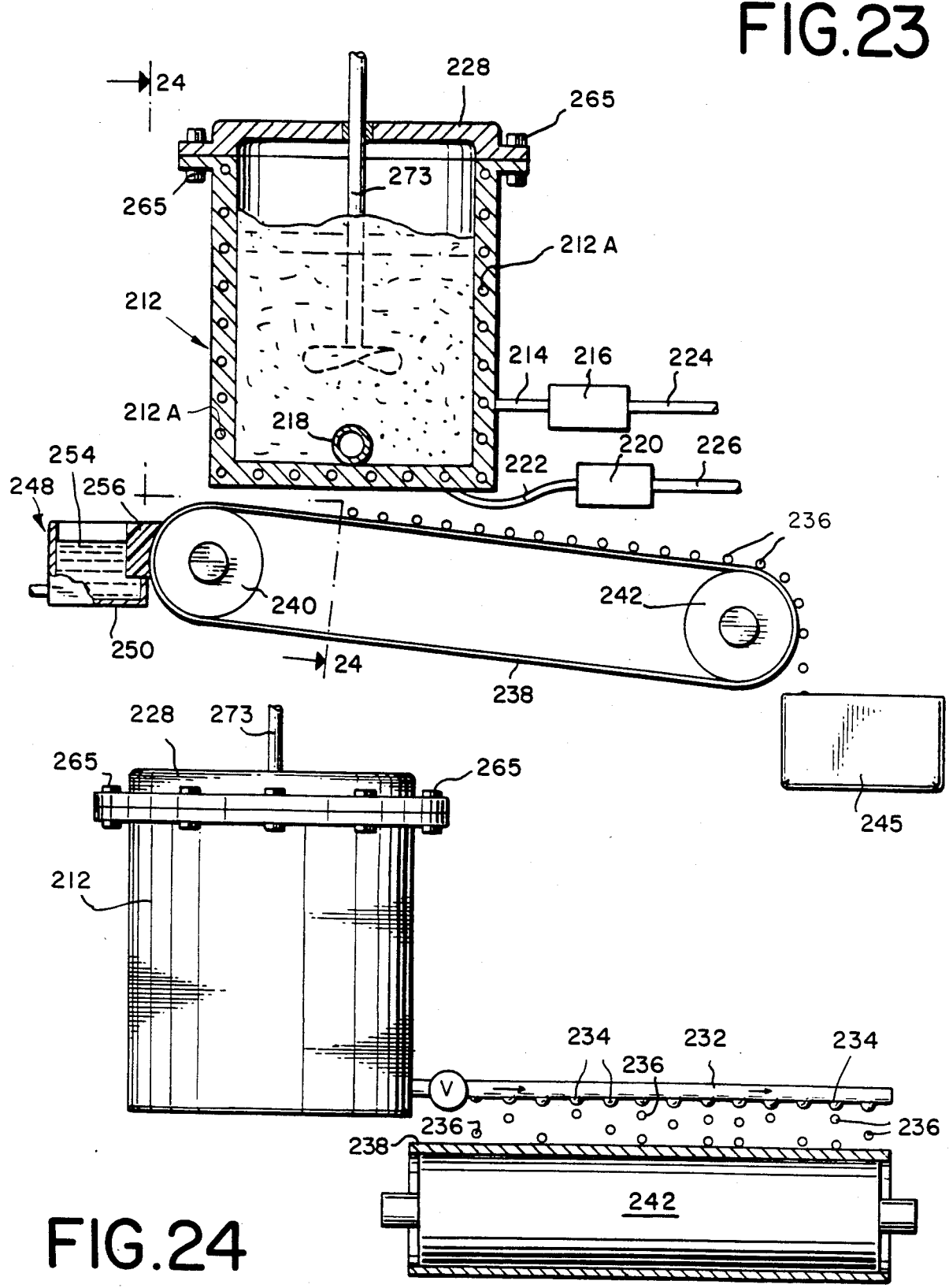

ETHER CARBOXALDEHYDES

This is a divisional of application Ser. No. 673,105, filed 11/19/84 now abandoned, which, in turn, is a divisional of application for U.S. Letters Patent, Ser. No. 533,915 filed on 9/19/83 and now U.S. Pat. No. 4,532,364; which, in turn, is a continuation-in-part of application for U.S. Letters Patent, Ser. No. 507,292 filed on 8/1/83, now abandoned.

BACKGROUND OF THE INVENTION

The instant invention provides ether carboxaldehydes defined according to the generic structure:

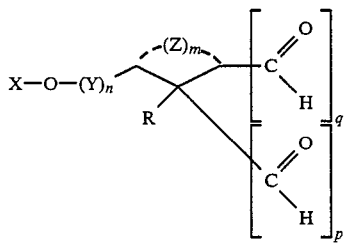

wherein X represents aryl, alkaryl, hydroxyalkyl, alkenyl, cycloalkenyl, lower alkyl or bicycloalkyl; wherein Y represents $C_1$–$C_3$ lower alkylene; wherein Z completes an alkyl substituted $C_6$ cycloalkyl ring or represents no moiety; wherein R represents hydrogen or methyl; wherein m represents 0 or 1; wherein n represents 0 or 1; wherein p represents 0 or 1 and wherein q represents 0 or 1 with the provisos that when m is 1, Z completes the alkyl substituted or unsubstituted $C_6$ cycloalkyl ring; that p is 1 when q is 0; and that when p is 0, q is 1, which are used to augment or enhance the aroma or taste of consumable materials.

Inexpensive chemical compositions of matter which can provide floral, lilac, carnation, green, herbaceous, ozoney, fruity, citrus, grapefruit-like, spicy, cinnamon-like, woody, patchouli, coriander, natural pine-like, cypress, fir balasam-like, calamus-like and diffusive saw dust aromas with caryophyllene-like and chocolate topnotes and fruity, woody, dry cedarwood and patchouli-like undertones are known and are highly desirable in the art of perfumery. Many of the natural materials which provide such fragrances and contribute desired nuances to perfumery compositions as well as perfumed articles including solid or liquid anionic, cationic, nonionic or zwitterionic detergents, perfumed articles, fabric softener compositions and fabric softener articles are high in cost, vary in quality from one batch to another and/or are generally subject to the usual variations of natural products.

By the same token, materials which can provide bitter orange and mango-like aromas and tastes are highly useful and are well known in the art of flavoring for foodstuffs, toothpastes, chewing gums, medicinal products and chewing tobaccos. Many of the natural materials which provide such flavor nuances and contribute desire nuances to flavor and compositions are high in cost, vary in quality from one batch to another and/or are generally subject to the usual variations of natural products.

Materials which are provide woody, green, herbaceous and spicy aroma and taste nuances to smoking tobacco compositions and components of smoking tobacco articles prior to and on smoking in the main stream and in the side stream are highly desirable in the smoking tobacco art. Many of the natural materials which provide such flavor and aroma nuances and contribute desired nuances to flavor and compositions for smoking tobacco and smoking tobacco article components, e.g., filters and wrappers as well as the main body of the tobacco are high in cost, vary in quality from one batch to another and/or are generally subject to the usual variations of natural products.

There is, accordingly, a continuing effort to find synthetic materials which will replace, enhance or augment the essential flavor and fragrance notes provided by natural essential oils or compositions thereof. Unfortunately, many of the synthetic materials eith have the desired nuances only to a relatively small degree, or else contribute undesirable or unwanted odor to the compositions. The search for materials which provide, for example, a more refined mango-like flavor, or a more refined cranberry flavor in cranberry sauce, for example, has been difficult and relatively costly in the areas of both natural products and synthetic products. By the same token, the search for materials which can provide a more refined lavender-spike aroma, for example, has been difficult and relatively costly in the areas of both natural products and synthetic products.

Artificial flavoring agents for foodstuffs have received increasing attention in many years. For many years, such food flavoring agents have been preferred over natural flavoring agents at least, in part, due to their diminished cost and their reproducable flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and deserts and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums, toothpastes and chewing tobaccos is not completely known. This is noticeable in products having mango-like and bitter orange flavor characteristics particularly.

Even more desirable are products that can serve to substitute for difficult-to-obtain natural perfumery oils and at the same time sustitute for natural flavoring ingredients in foodstuffs, chewing gums, medicinal products, toothpastes, chewing tobaccos, smoking tobaccos and smoking tobacco article components.

Oxo reaction products are well known in the art of perfumery. Thus, U.S. Pat. No. 4,374,277 issued on Feb. 15, 1983, the specification of which is incorporated by reference herein describes branched chain $C_{11}$ aldehydes and alcohols, processes for producing same by (i) first dimerizing isoamylene (2-methyl-2-butene) to form a mixture of diisoamylenes and (ii) reacting the resulting mixture or separated components thereof with carbon monoxide and hydrogen by means of an oxo reaction, as well as methods for augmenting or enhancing the aroma of perfumes, colognes and perfumed articles by adding thereto aroma augmenting or enhancing quantities of the thus produced $C_{11}$ branched chain aldehydes and alcohol compositions of matter.

Furthermore, ether carboxaldehydes are well known in the art of perfumery for augmenting or enhancing the aroma of perfume compositions or perfumed articles. Thus, U.S. Pat. No. 4,359,390 issued on Nov. 16, 1982, the specification for which is incorporated by reference herein discloses the use of such ether carboxaldehydes as the compound having the structure:

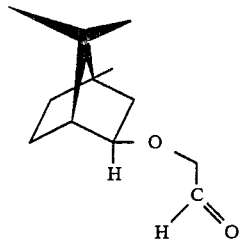

in augmenting or enhancing the aroma of perfume compositions, colognes and perfumed articles (e.g., perfume plastics, solid or liquid anionic, cationic, nonionic or zwitterionic detergents, fabric softener compositions or drier-added fabric softener articles.

Nothing in the prior art however, suggest the ether carboxaldehydes of our invention, or the products produced according to the processes which comprise reacting the allylic ethers with carbon monoxide and hydrogen via an oxo reaction to produce compositions of matter containing a major proportions of such ether carboxaldehydes of our invention or the organoleptic uses of same.

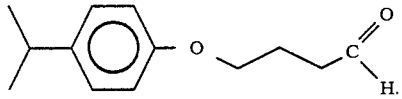

Figure 2:
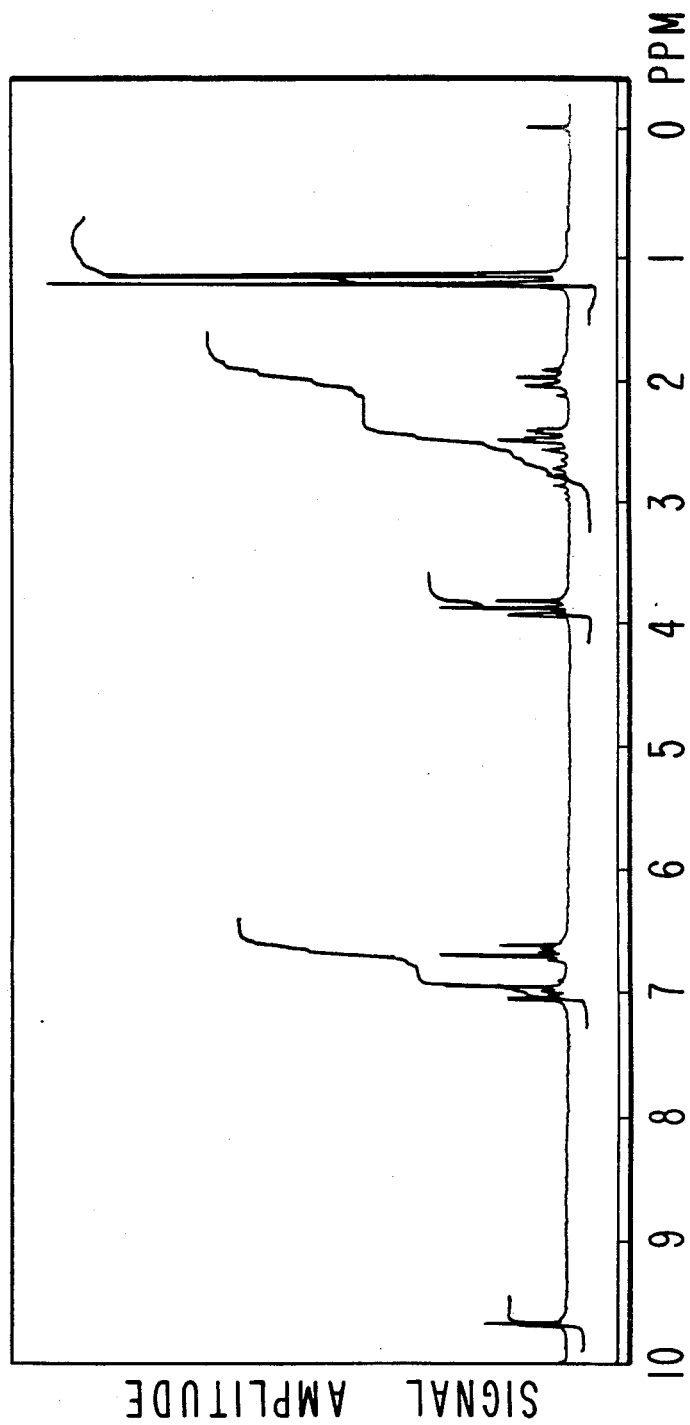

FIG. 2 is the NMR spectrum for the compound having the structure:

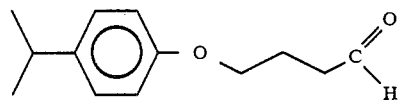

produced according to Example I (conditions: Field strength 100 MHz; solvent: $CFCl_3$)

Figure 3:
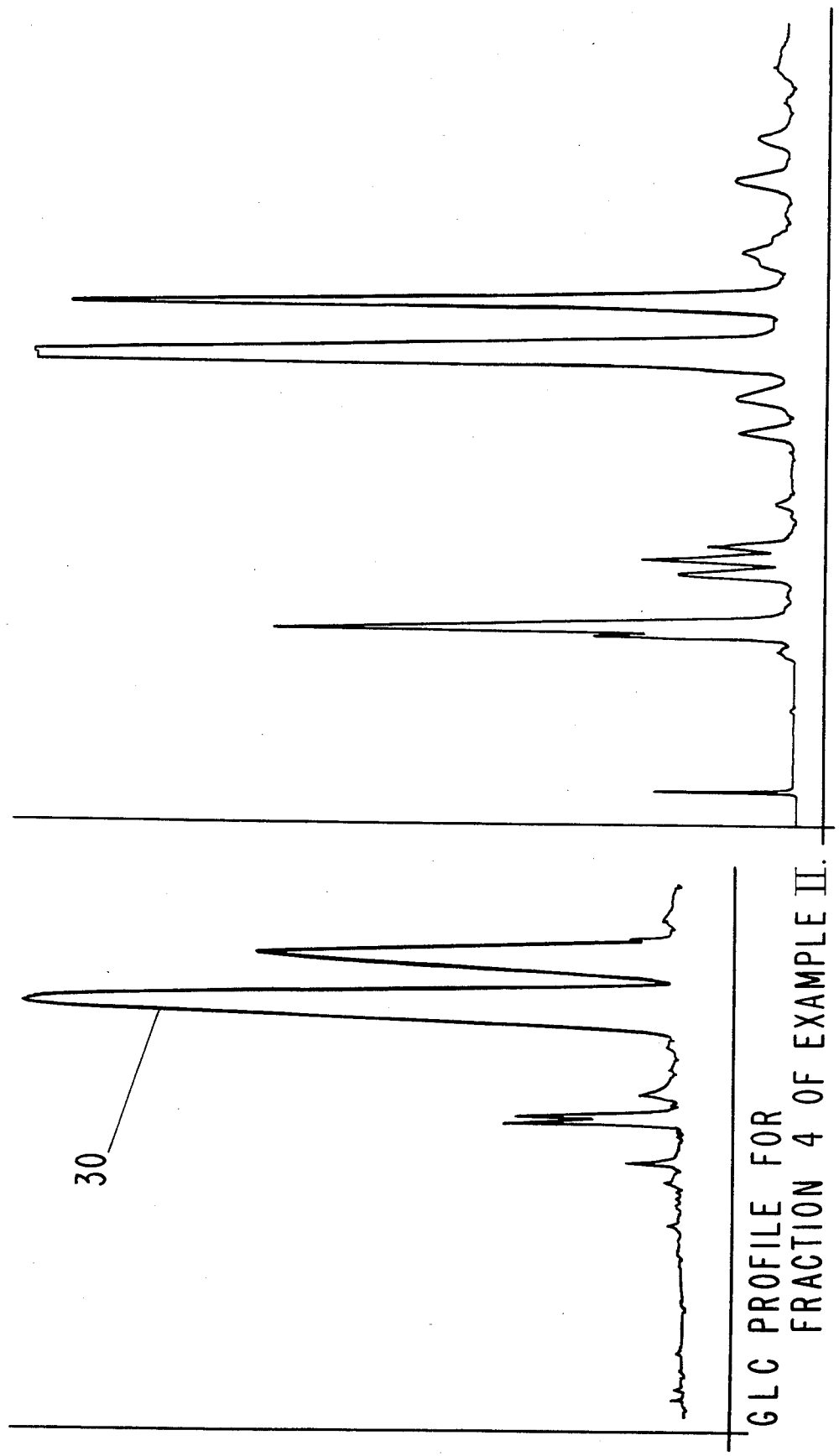

FIG. 3 is the GLC profile for fraction 4 of the distillation product of the reaction product of Example II containing the compound having the structure:

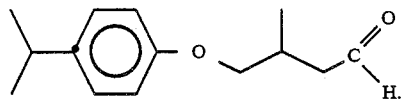

Figure 4:
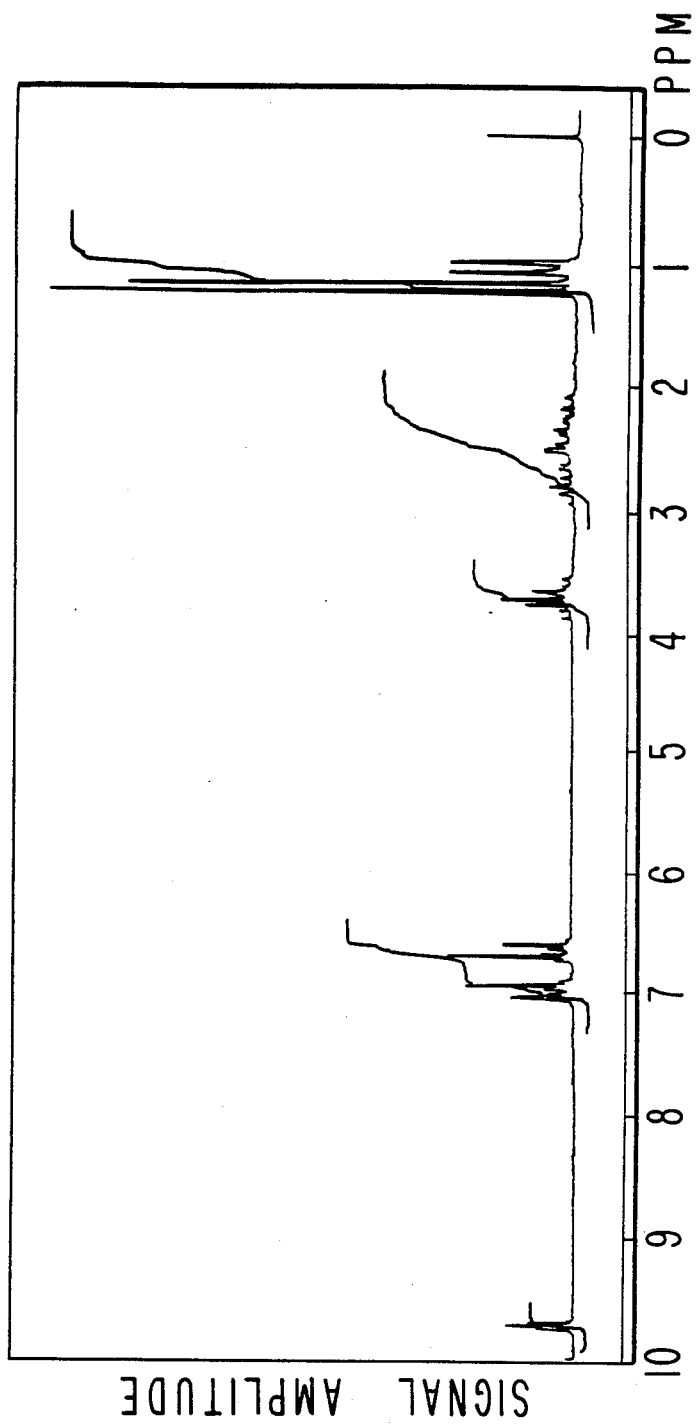

FIG. 4 is the NMR spectrum for the peak indicated by reference numeral "30" on FIG. 3 which is the GLC profile for fraction 4 of the distillation product of the reaction product of Example II containing the compound having the structure:

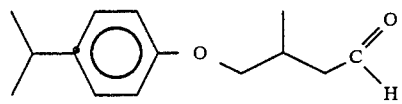

(Conditions: Field strength 100 MHz; solvent: $CFCl_3$).

FIG. 5 is the GLC profile for bulked fractions 2–4 of the first distillation product of the reaction product of Example III containing the compound having the structure:

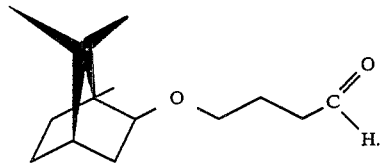

Figure 6:
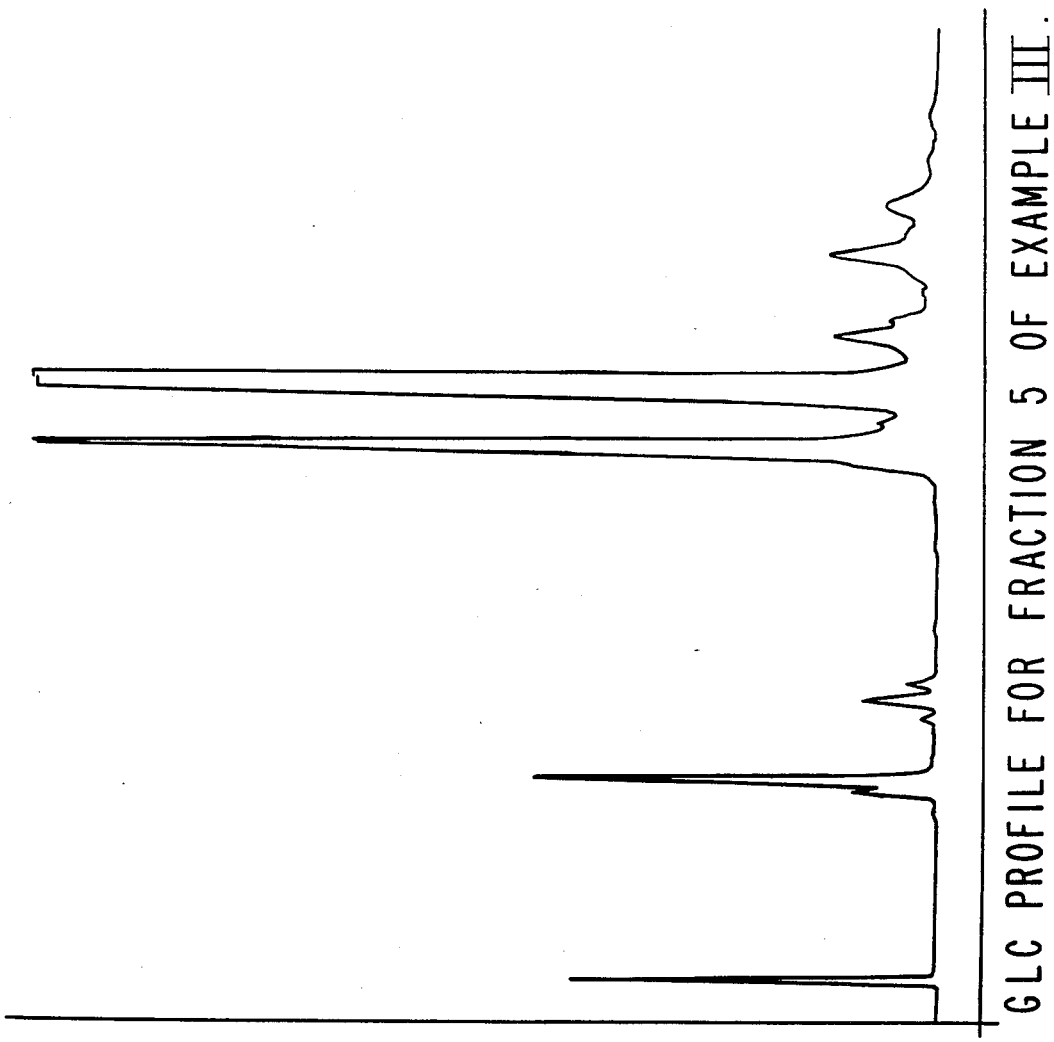

FIG. 6 is the GLC profile for fraction 5 of the second distillation product of the reaction product of Example III containing the compound having the structure:

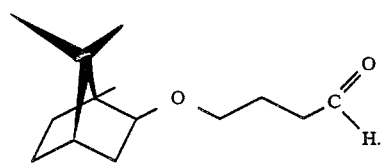

FIG. 7 is the NMR spectrum for the compound having the structure:

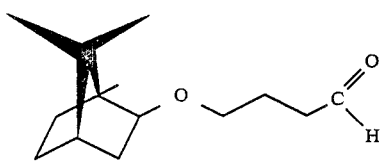

produced according to Example III (conditions: Field strength 100 MHz; solvent: $CFCl_3$).

Figure 8:
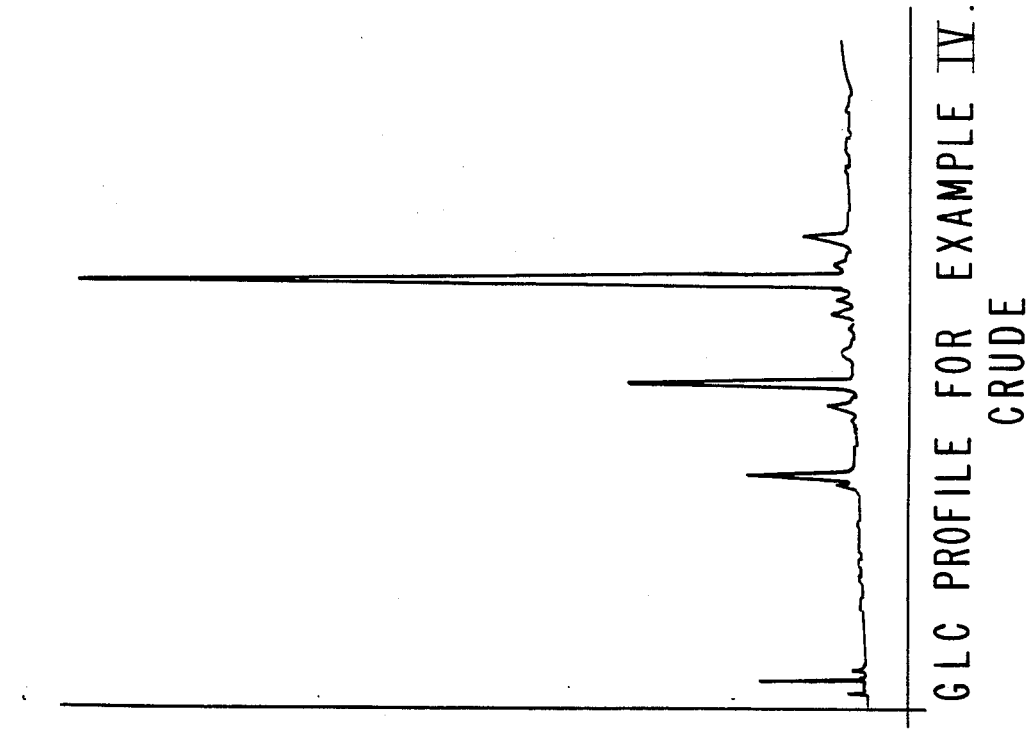

FIG. 8 is the GLC profile for the crude reaction product of Example IV containing the compound having the structure:

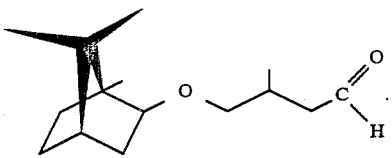

Figure 9:
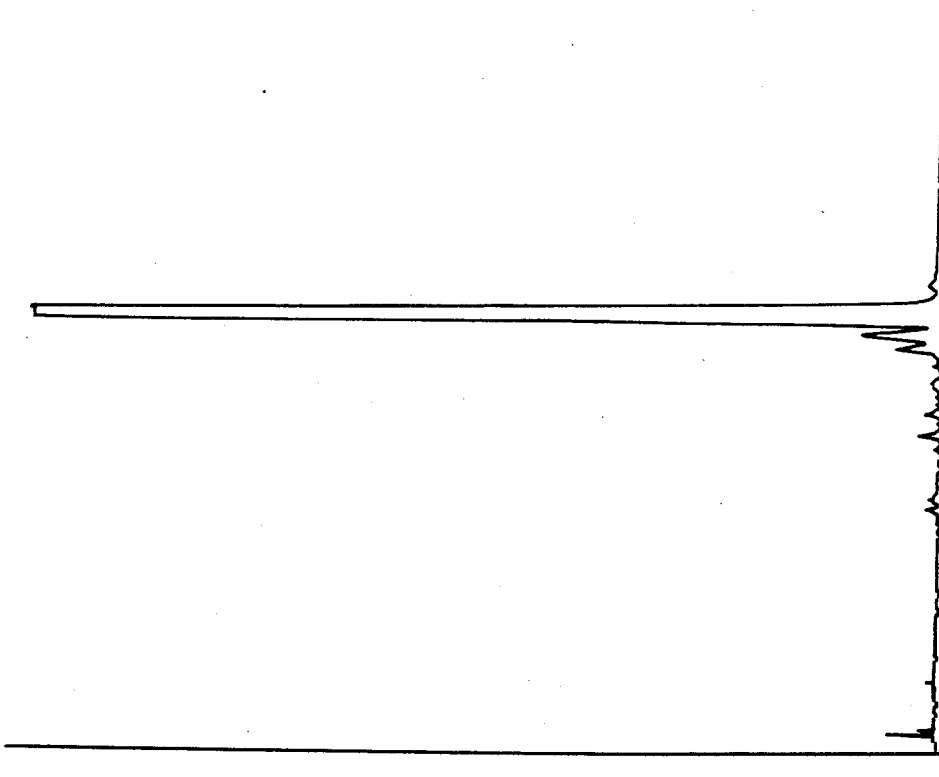

FIG. 9 is the GLC profile for fraction 6 of the distillation product of the reaction product of Example IV containing the compound having the structure:

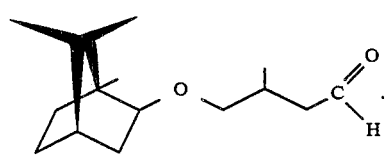

Figure 10:
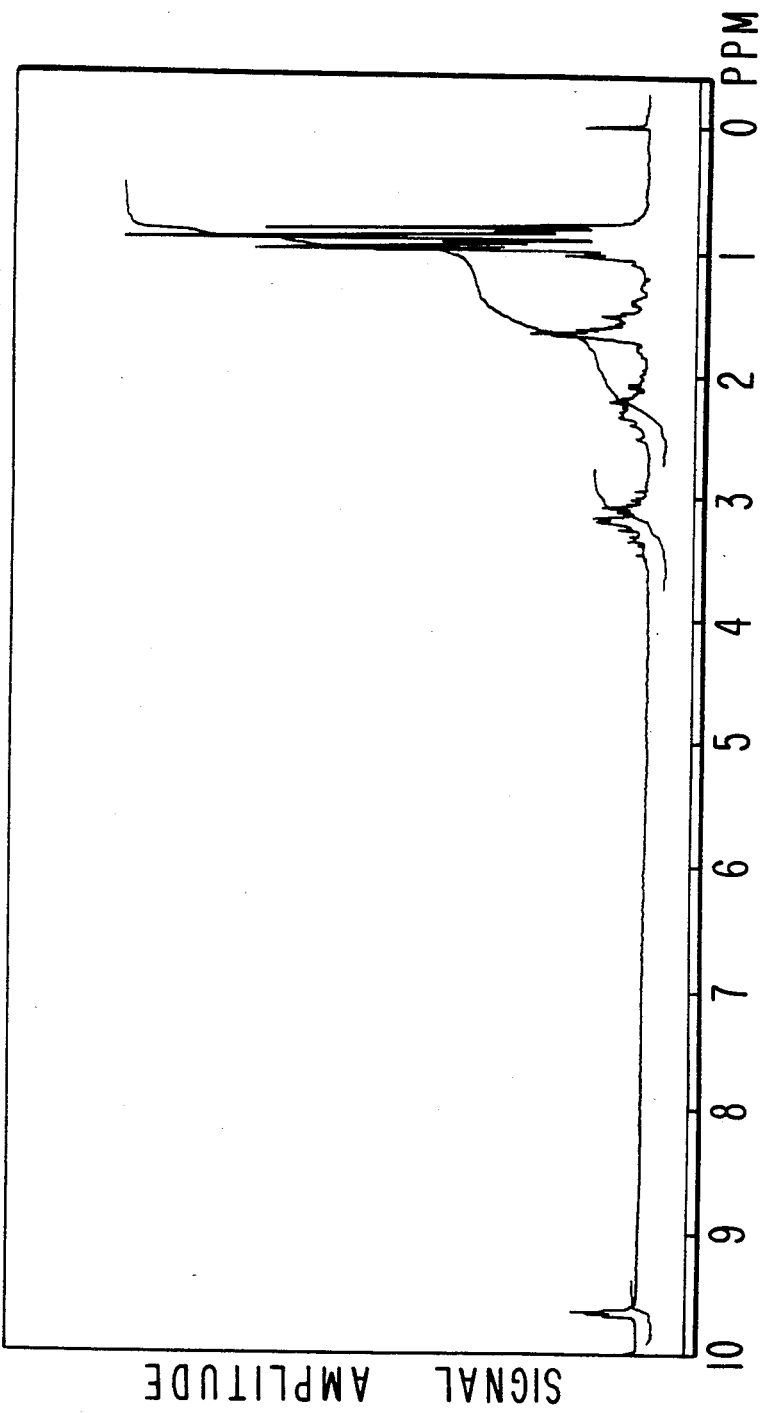

FIG. 10 is the NMR spectrum for fraction 6 of the distillation product of the reaction product of Example IV containing the compound having the structure:

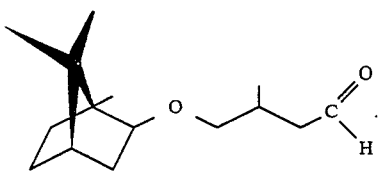

Figure 11:
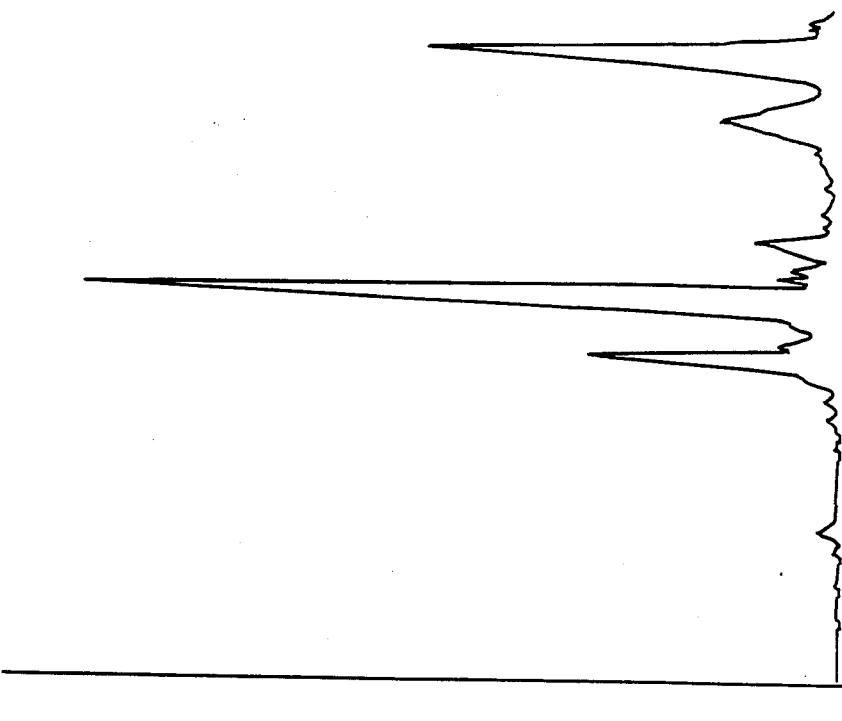

FIG. 11 is the GLC profile for fraction 4 of the first distillation product of the reaction product of Example V containing the compound having the structure:

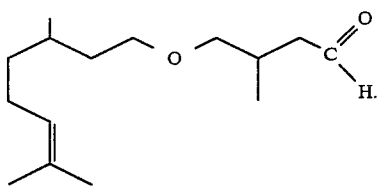

Figure 12:
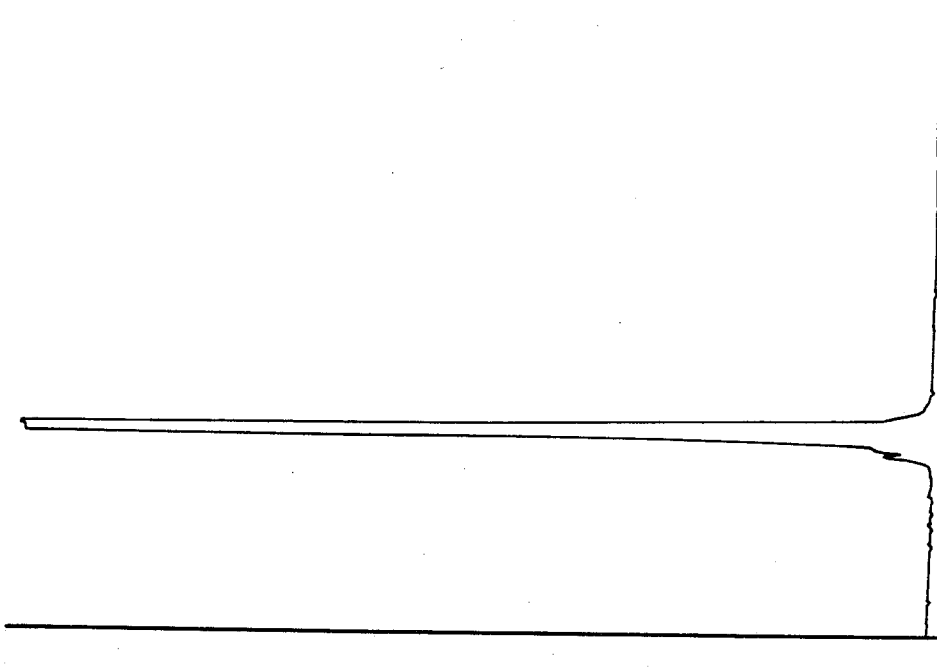

FIG. 12 is the GLC profile for fraction 19 of the final distillation product of the reaction product of Example V containing the compound having the structure:

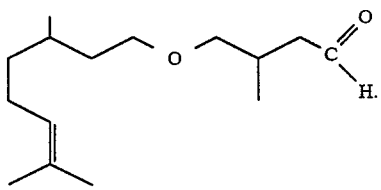

Figure 13:
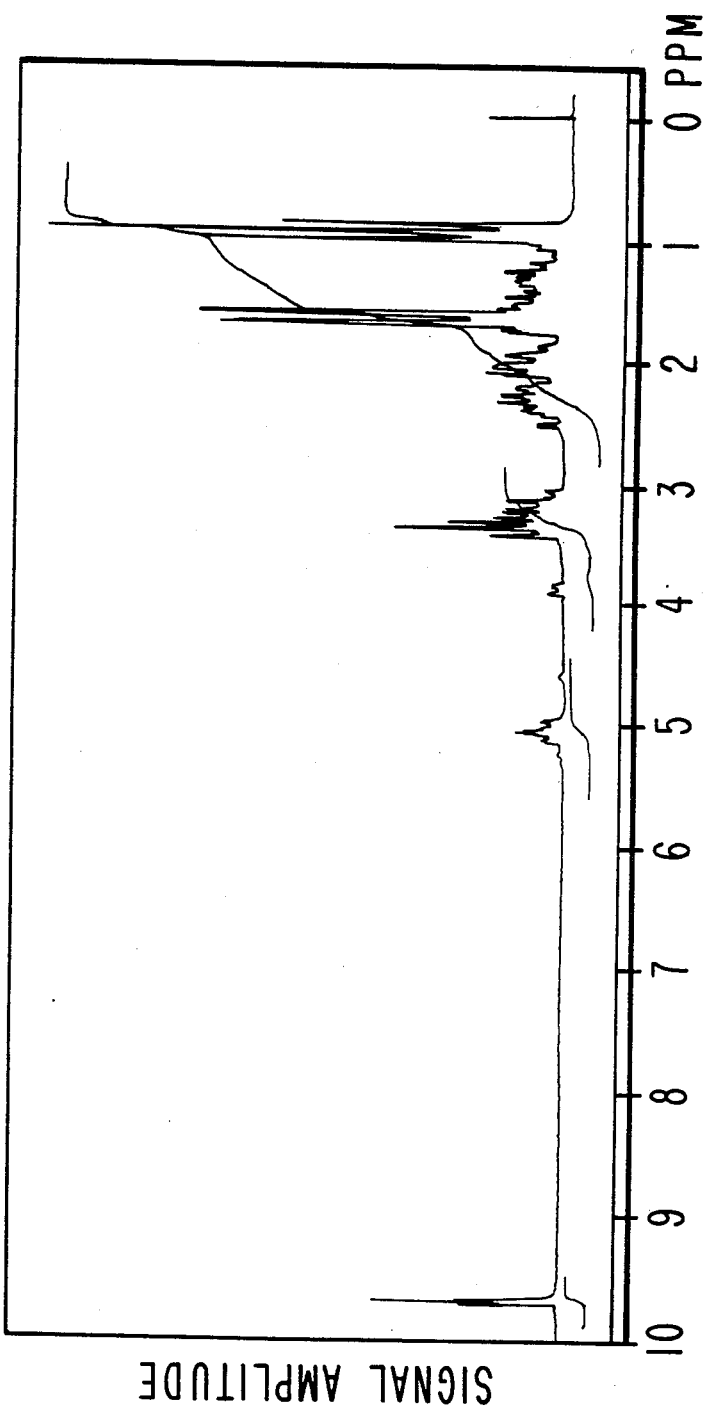

FIG. 13 is the NMR spectrum for fraction 19 of the final distillation product of the reaction product of Example V containing the compound having the structure:

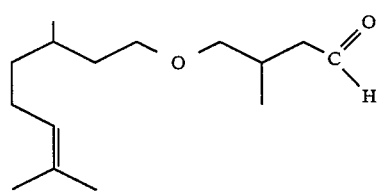

(conditions: Field strength 100 MHz; solvent: CFCl₃).

Figure 14:
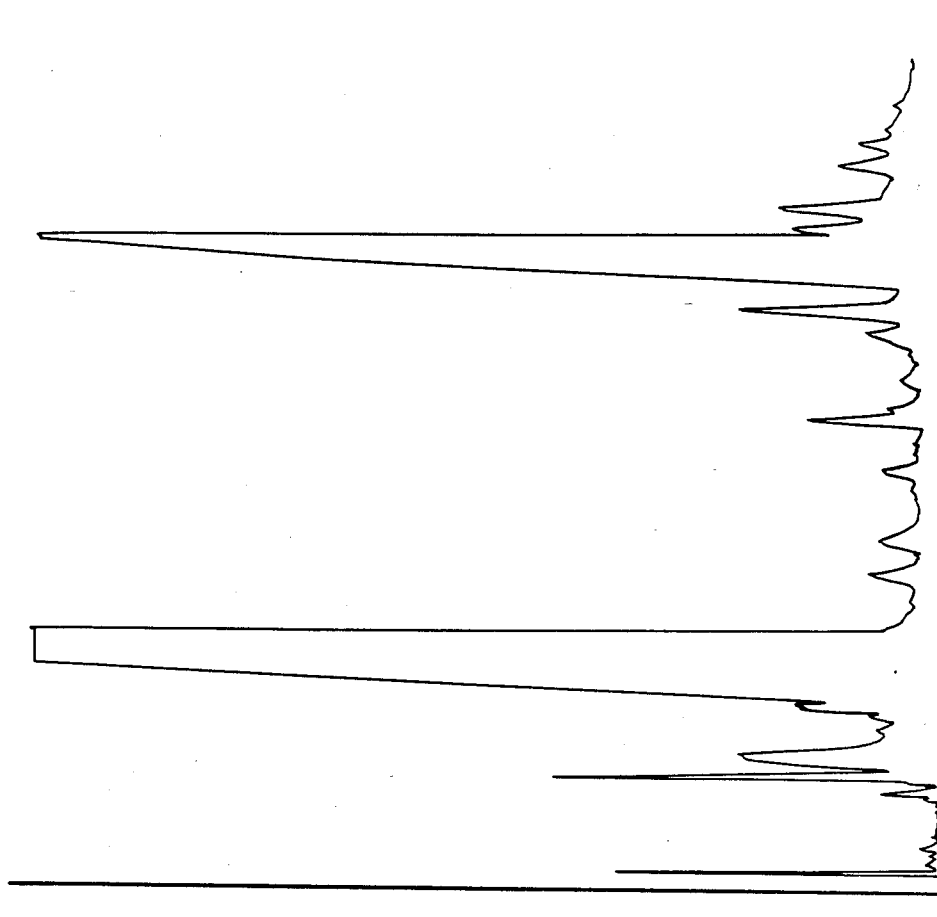

FIG. 14 is the GLC profile for the crude reaction product of Example VI containing the compound having the structure:

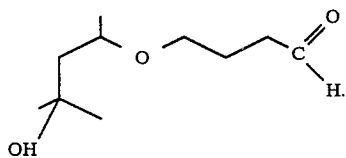

Figure 15:
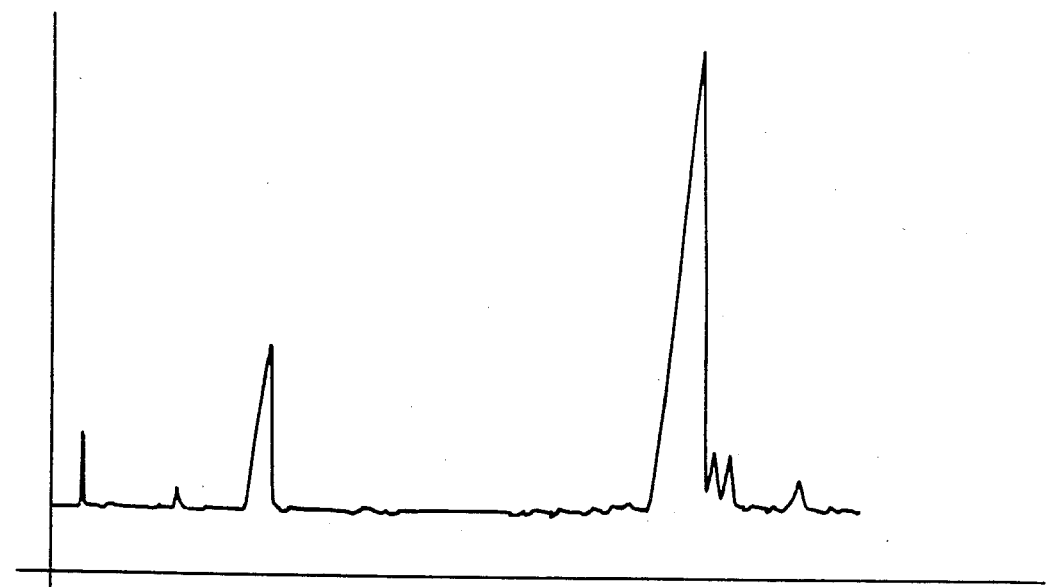

FIG. 15 is the GLC profile for fraction 9 of the distillation product of the reaction product of Example VI containing the compound having the structure:

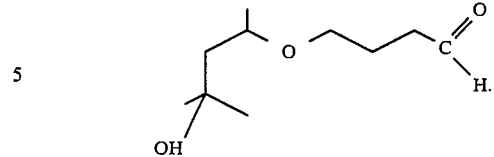

Figure 16:
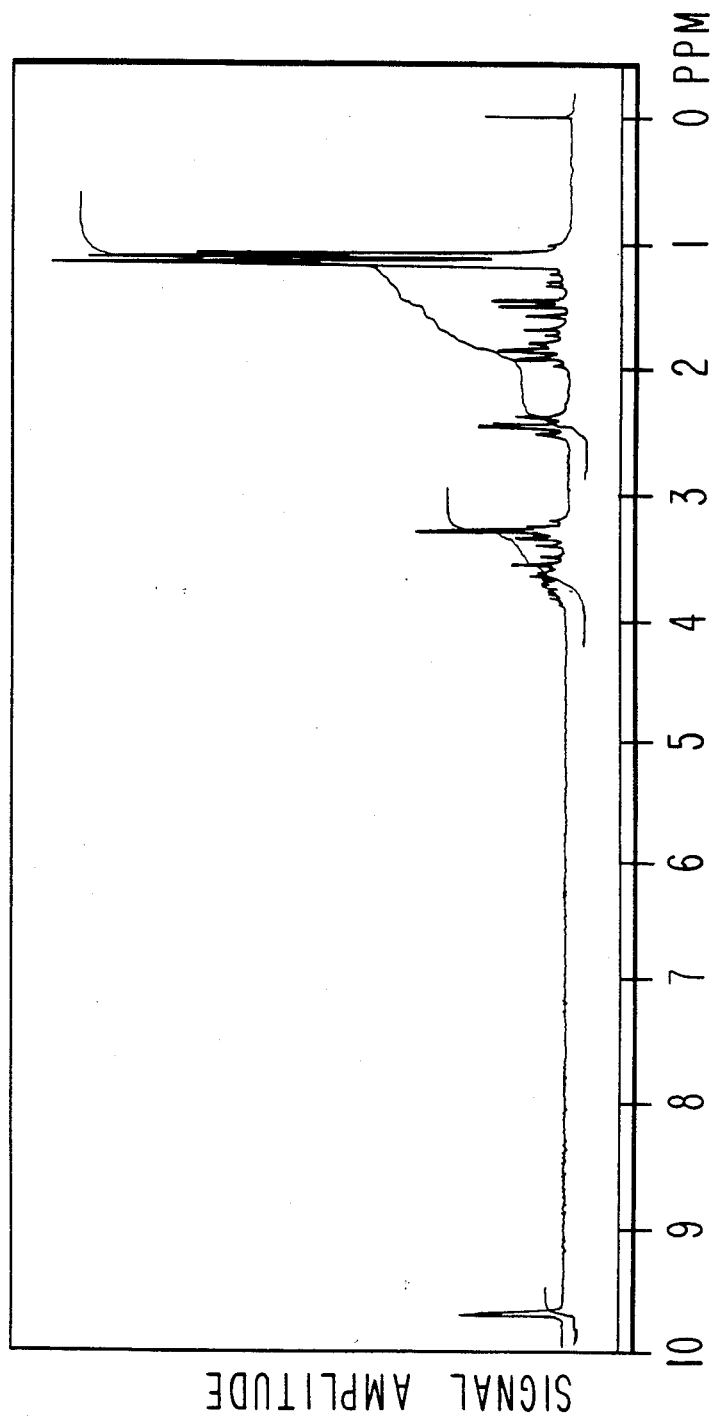

FIG. 16 is the NMR spectrum for fraction 9 of the distillation product of the reaction product of Example VI containing the compound having the structure:

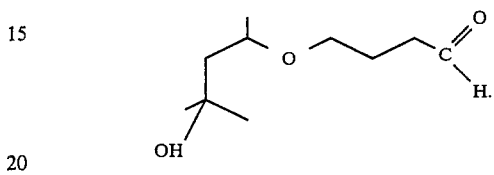

FIG. 17 is the GLC profile for the crude reaction product of Example VII containing the compound having the structure:

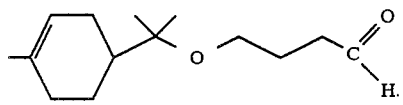

Figure 18:
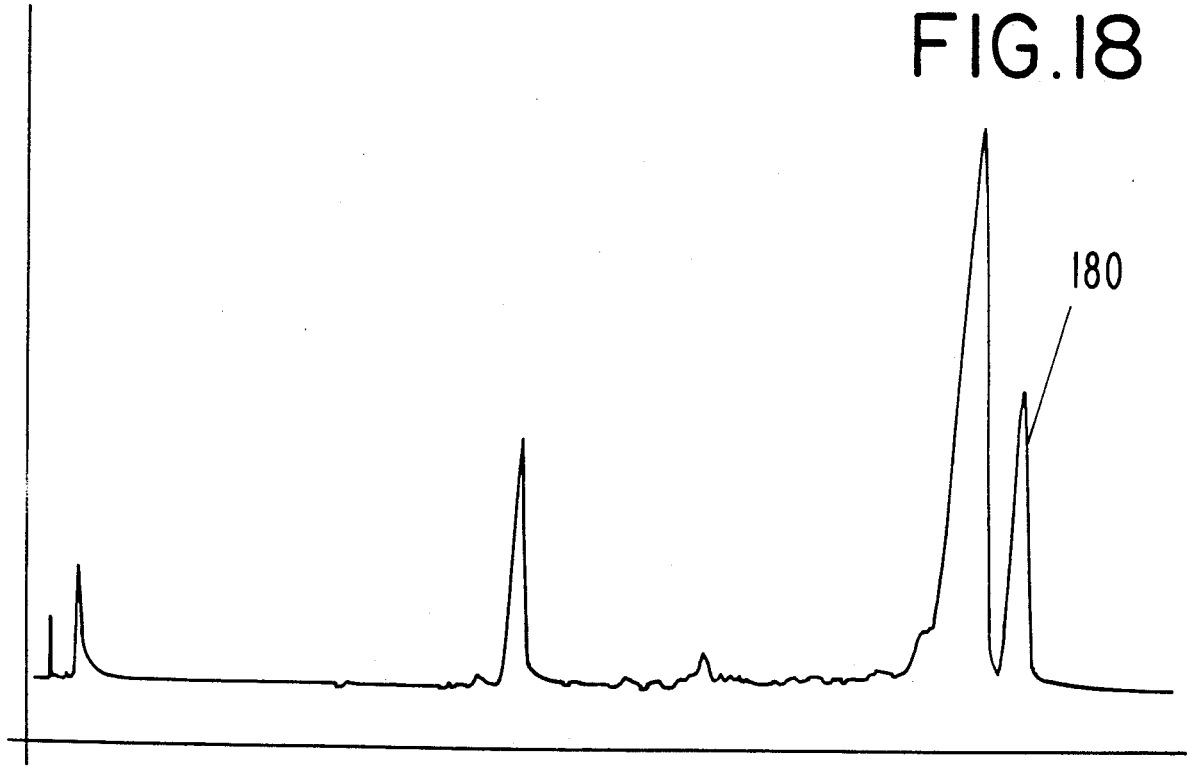

FIG. 18 is the GLC profile for fraction 11 of the distillation product of the reaction product of Example VII containing the compound having the structure:

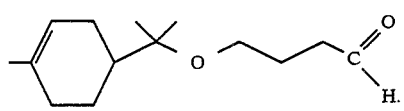

Figure 19:
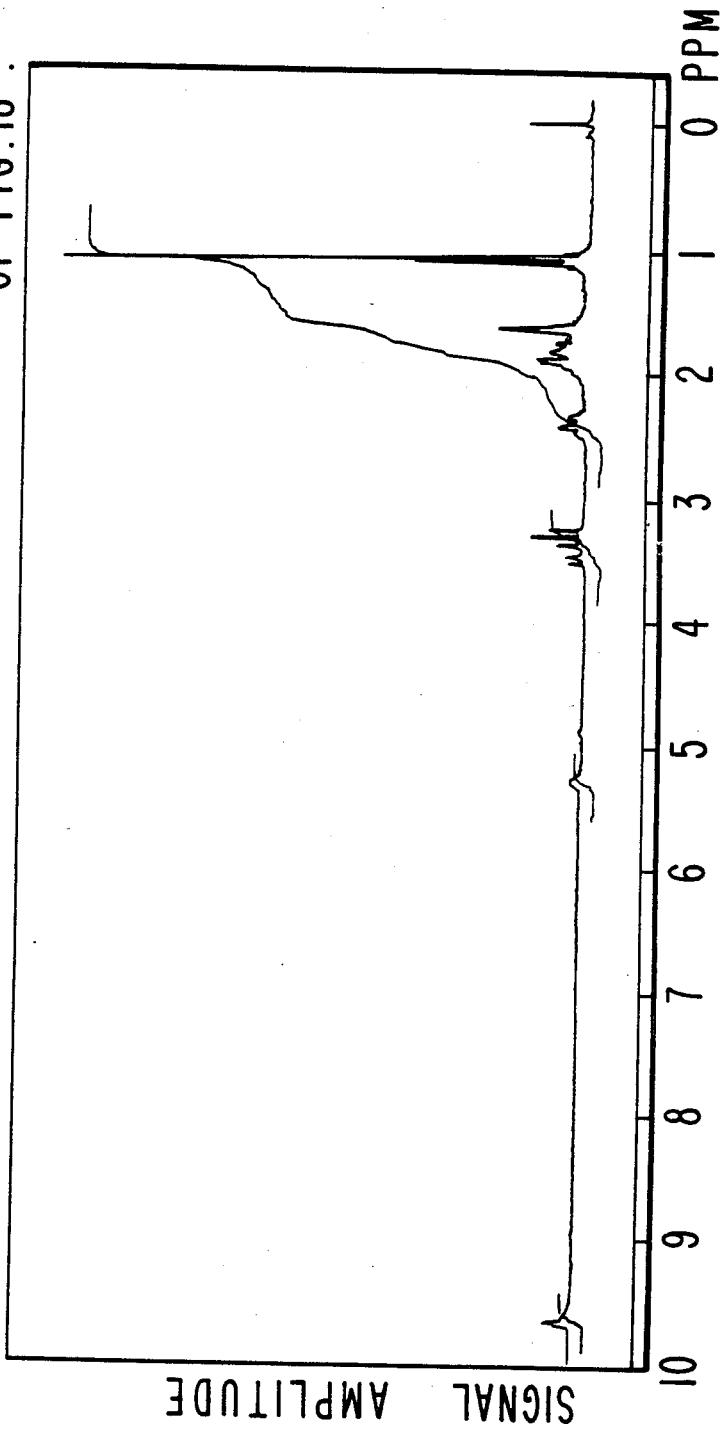

FIG. 19 is the NMR spectrum for peak "180" of FIG. 18, the GLC profile for fraction 11 of the distillation product of the reaction product of Example VII containing the compound having the structure:

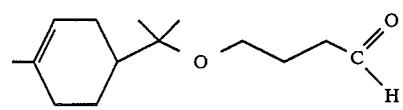

(Conditions: Field strength 100 MHz; solvent: CFCl₃).

Figure 20:
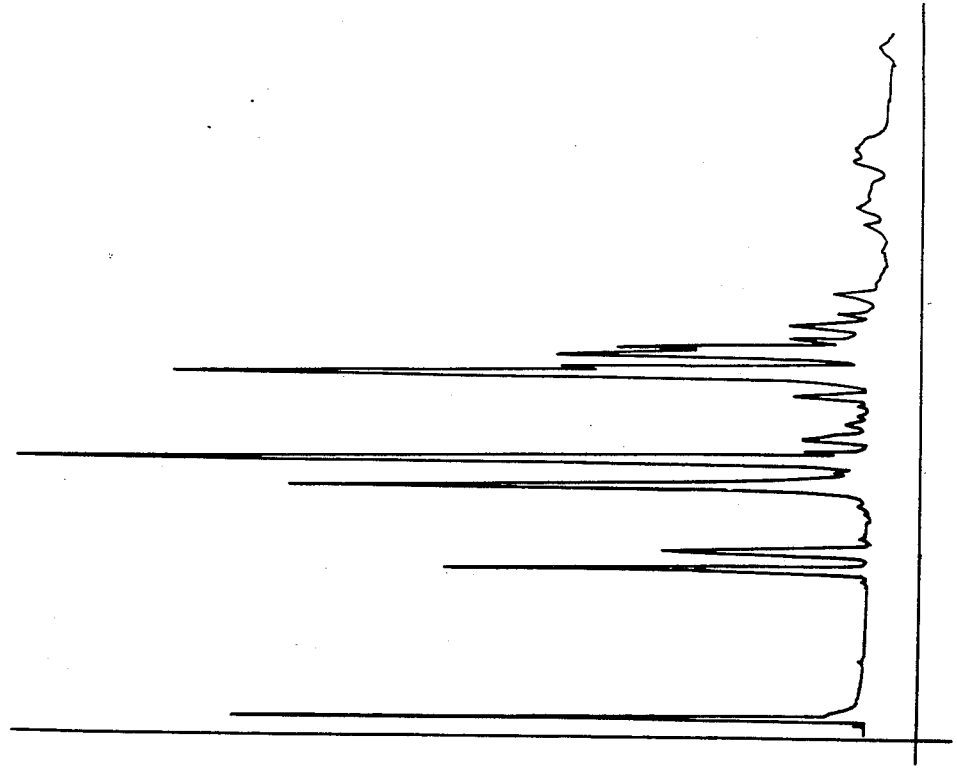

FIG. 20 is the GLC profile for the crude reaction product of Example VIII containing the compound having the structure:

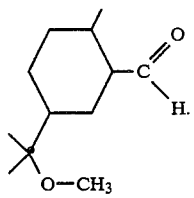

Figure 21:
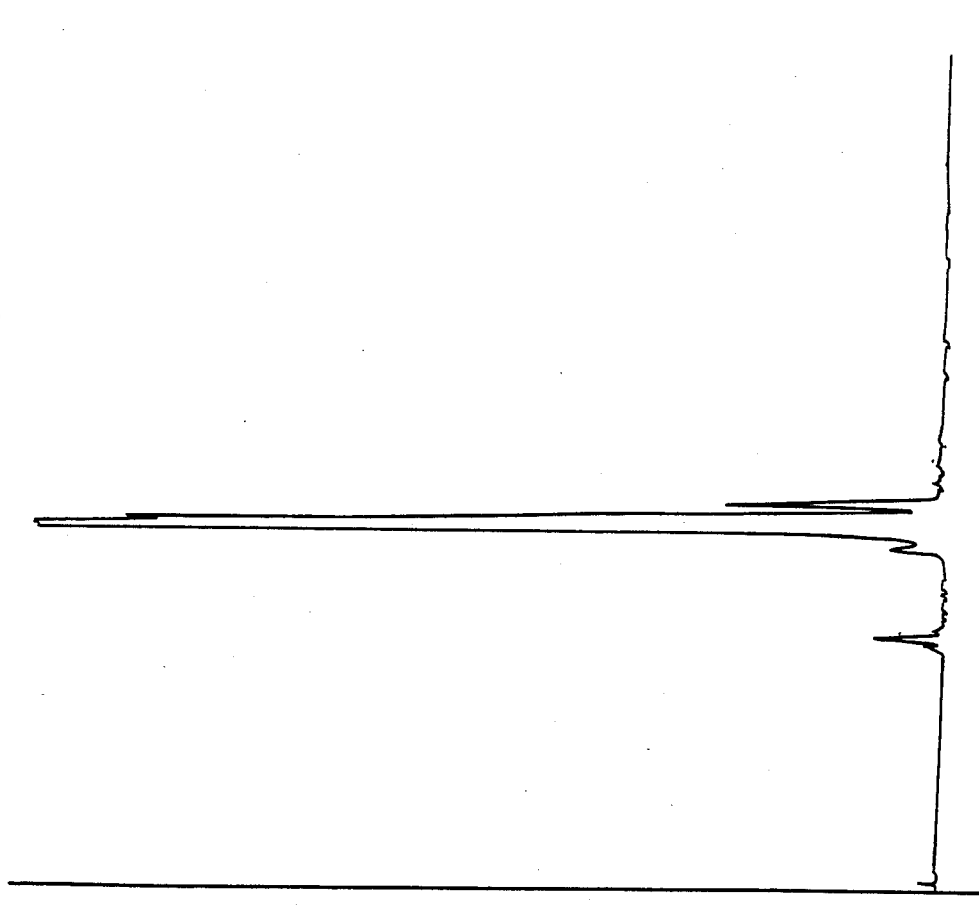

FIG. 21 is the GLC profile for fraction 8 of the distillation product of the reaction product of Example VIII containing the compound having the structure:

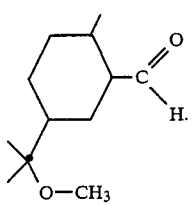

Figure 22:
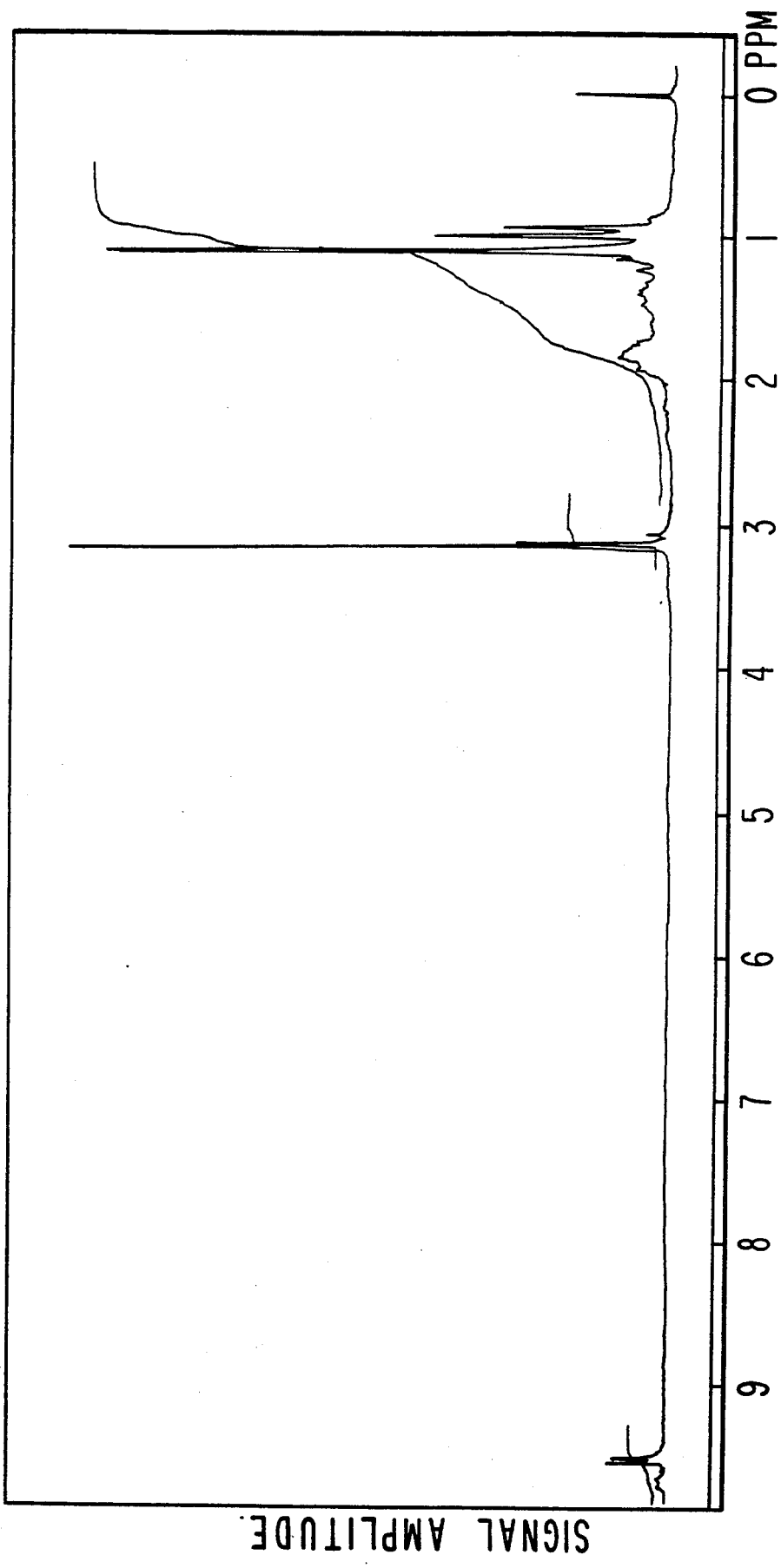

FIG. 22 is the NMR spectrum for the compound having the structure:

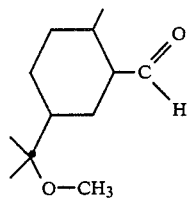

produced according to Example VIII (conditions: Field strength: Field strength: 100 MHz; Solvent: CFCl₃).

FIG. 23 represents a cut-away side elevation view of apparatus used in forming perfumed polymers which contain imbedded therein at least one of the ether carboxaldehydes of our invention.

FIG. 24 is a front view of the apparatus of FIG. 23 looking in the direction of the arrows.

DETAILED DESCRIPTION OF THE DRAWINGS

Figure 1:
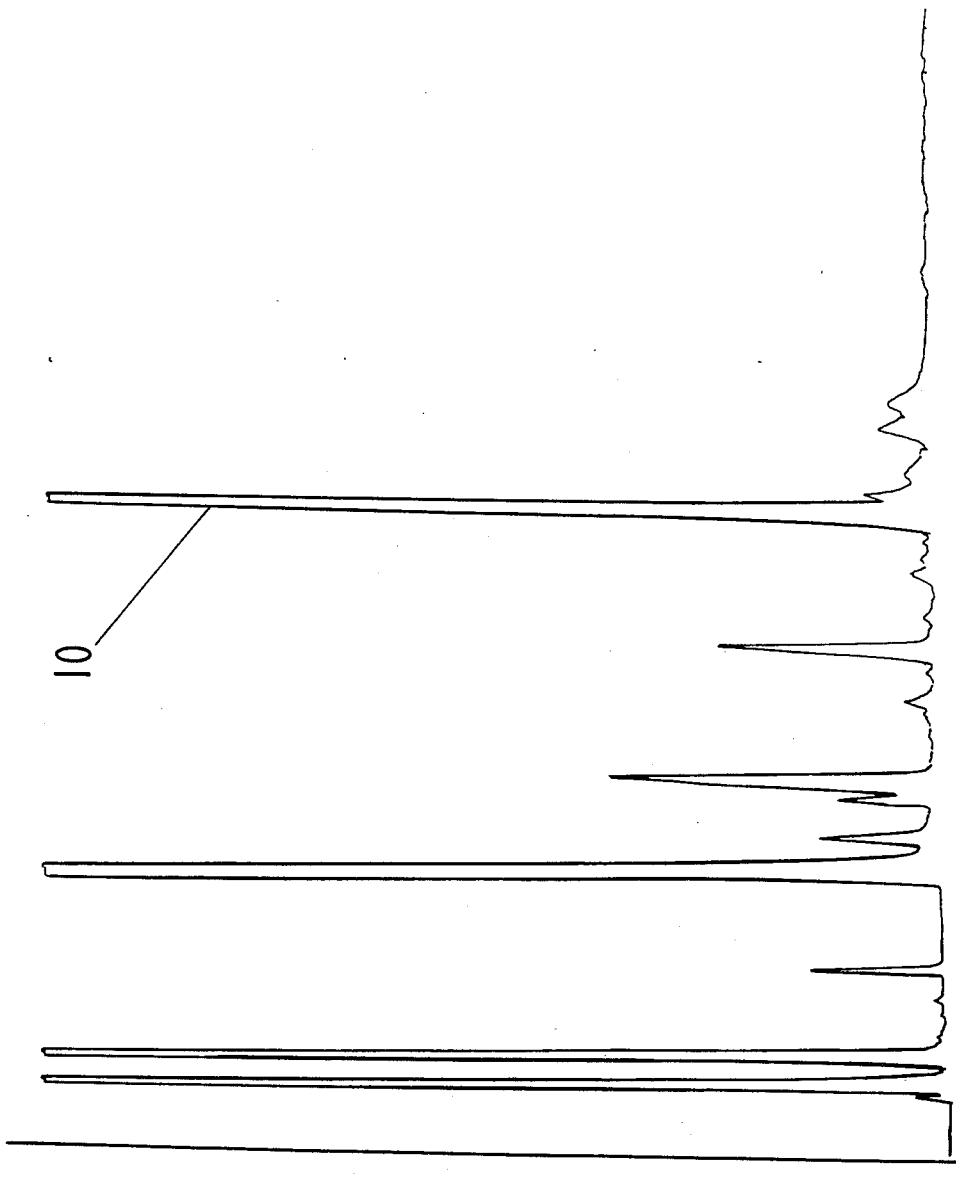
FIG. 1 is the GLC profile for the crude reaction product of Example I containing the compound having the structure.

FIG. 1 is the GLC profile for the crude reaction product produced according to Example I containing the compound having the structure:

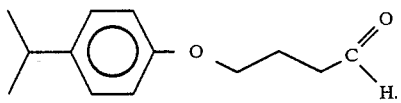

The peak indicated by reference numeral "10" is the peak for the compound having the structure:

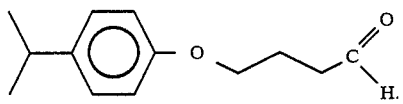

FIG. 3 is the GLC profile for fraction 4 of the distillation product of the reaction product of Example II containing the compound having the structure:

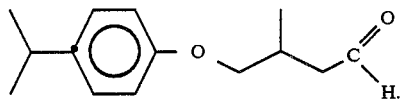

The peak indicated by reference numeral "30" is the peak for the compound having the structure:

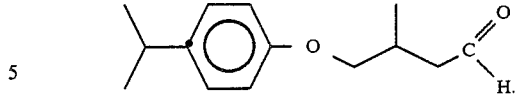

FIG. 18 is the GLC profile for fraction 11 of the distillation product of the reaction product of Example VII containing the compound having the structure:

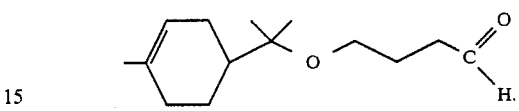

The peak indicated by reference numeral "180" is the peak for the compound having the structure:

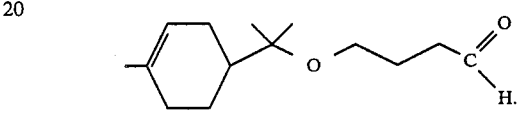

Referring to FIGS. 23 and 24, there is provided a process for forming scented polymer elements (wherein the polymer may be thermoplastic polymers such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 23 and 24, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the ether carboxaldehydes or our invention or mixtures of ether carboxaldehydes and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212A having heated coils which are supplied with electric current through cable 214 from a rheostat or control 216 is operated to maintain the temperature inside the container 212 such that the polymer in the container will be maintained in the molten or liquid state. It has been found advantageous to emply polymers at such a temperature that the viscosity will be in the range of 90-100 sayboldt seconds. The heater 218 is operated to maintain the upper portion of the container 212 within a temperature range of, for example, 220°-270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 is heated from 10-12 hours, whereafter the perfume composition or perfume material which contains one or more of the ether carboxaldehydes of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the ether carboxaldehydes of our invention or mixture of perfume substance and one or more of the ether carboxaldehydes of our invention, will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is all of or which contains one or more of the ether carboxaldehydes of our invention, through the orifices 234 at a rate which will insure the formation of droplets 236 which will fall downwardly onto a moving conveyor belt 238 caused to run between conveyor wheels 240 and 242 beneath the conduit 232.

Then the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides compounds having the generic structure:

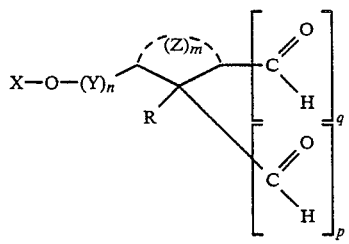

wherein X represents aryl, alkaryl, hydroxyalkyl, alkenyl, cycloalkenyl, lower alkyl or bicycloalkyl; wherein Y represents $C_1$-$C_3$ lower alkylene; wherein Z completes an alkyl substituted $C_6$ cycloalkyl ring or represents no moiety; wherein R represents hydrogen or methyl; wherein m represents 0 or 1; wherein n represents 0 or 1; wherein p represents 0 or 1 and wherein q represents 0 or 1 with the provisos that when m is 1, Z completes the alkyl substituted or unsubstituted $C_6$ cycloalkyl ring; that p is 1 when q is 0; and that when p is 0, q is 1. The present invention also provides a process for preparing such compounds by means of carrying out an oxo reaction on allyl ethers using carbon monoxide and hydrogen, the structure of the allyl ethers being:

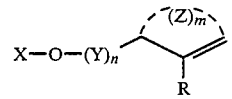

and the reaction being:

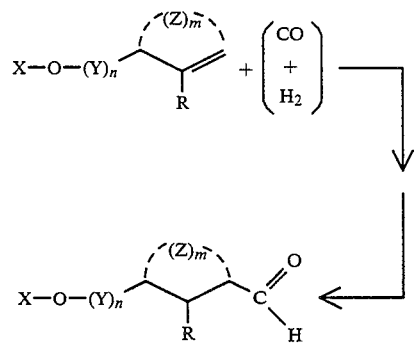

The present invention also provides products produced according to such process. The resulting compounds, ether carboxaldehydes of our invention produced according to the process of our invention are capable of augmenting or enhancing bitter orange and mango aromas and tastes of foodstuffs, chewing gums, toothpastes, medicinal products and chewing tobaccos.

The ether carboxaldehydes of our invention as well as mixtures thereof produced according to the process of our invention are also capable of modifying or enhancing the aroma characteristics of perfume compositions, colognes and perfumed articles (including soaps, anionic, cationic, nonionic or zwitterionic detergents, fabric softener compositions, optical brightener compositions and drier-added fabric softener articles) and perfumed polymers by imparting thereto floral, lilac, carnation, green, herbaceous, ozoney, fruity, citrus, grapefruit, spicy, cinnamon-like, woody, patchouli, coriander, natural pine-like, cypress, fir balsam-like, calamus-like and diffusive saw dust aromas with caryophyllene and chocolate topnotes and fruity, woody, dry cedarwood and patchouli-like undertones, thus fulfilling a need in the field of perfumery and detergent and cosmetics manufacture.

In smoking tobacco, smoking tobacco flavoring compositions, substitute smoking tobacco and substitute smoking tobacco flavoring compositions, the ether carboxaldehydes of our invention produced according to the process of our invention impart woody, green, herbaceous and spicy aroma and taste nuances both prior to and on smoking in the main stream and in the side stream.

The ether carboxaldehydes of our invention defined according to the structure:

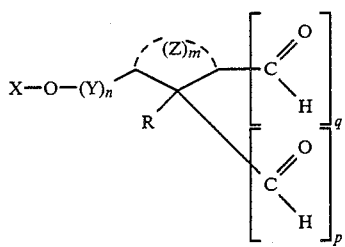

wherein X represents aryl, alkaryl, hydroxyalkyl, alkenyl, cycloalkenyl, lower alkyl or bicycloalkyl; wherein Y represents $C_1$-$C_3$ lower alkylene; wherein Z completes an alkyl substituted $C_6$ cycloalkyl ring or represents no moiety; wherein R represents hydrogen or methyl; wherein m represents 0 or 1; wherein n represents 0 or 1; wherein p represents 0 or 1 and wherein q represents 0 or 1 with the provisos that when m is 1, Z completes the alkyl substituted or unsubstituted $C_6$ cycloalkyl ring; that p is 1 when q is 0; and that when p is 0, q is 1, are prepared by first reacting allyl ethers defined according to the structure:

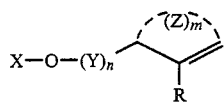

with carbon monoxide and hydrogen (carrying out a "oxo" reaction).

The allyl ethers defined according to the structure:

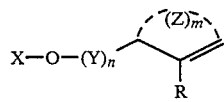

may be prepared by means of any standard ether synthesis, e.g., a "Williamson" synthesis or a synthesis as set forth in U.S. Pat. No. 4,163,068 issued on July 31, 1979, the specification for which is incorporated by reference herein. Thus, the ethers so useful in our invention may be formed by reacting an alcohol with another alcohol, for example, an allylic alcohol in the presence of an acid catalyst such as para toluene, sulphonic acid at reflux conditions. The reaction mass is refluxed for a period of from two hours up to ten hours, after which a period of time the reaction product is separated from the reaction mass as by distillation.

The ethers so useful in practicing our invention may also be formed by reacting the corresponding alcohol with an appropriate allylic halide or other organic halide as the case may be. This reaction is carried out under the influence of base comprising the step of placing the reactants for the process and the base, respectively, in two immiscible phase; an organic phase and either (i) an aqueous base phase or (ii) a solid base phase with the reactants being located substantially entirely in the first mentioned organic phase and the base being located substantially entirely in the second mentioned phase; and adding to the two phase system a "phase transfer agent" which may be one or more of several organic quaternary ammonium salts.

Specific examples of "phase transfer agents" useful in our invention are as follows:
Tricapryl methyl ammonium chloride;
Cetyl trimethyl ammonium bromide; and
Benzyl trimethyl ammonium hydroxide.
In general, the "phase transfer agents" most preferred have the generic formula:

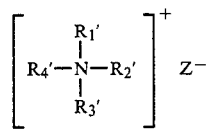

wherein at least one or $R_1'$, $R_2'$, $R_3'$ and $R_4'$ is $C_6$-$C_{14}$ aryl, $C_6$-$C_{10}$ aralkyl, $C_6$-$C_{20}$ alkyl, $C_6$-$C_{14}$ aralkyl and $C_6$-$C_{20}$ alkenyl, and the other of $R_2'$, $R_3'$ and $R_4'$ is alkyl such as methyl, ethyl, n-propyl, i-propyl, 1-butyl, 2-butyl, 1-methyl-2-propyl, 1-pentyl and 1-octyl and Z- is an anion such as chloride, bromide and hydroxide.

This aspect of the process is carried out in an inexpensive solvent which is inert to the reaction system such as toluene, benzene, o-xylene, m-xylene, p-xylene, ethyl benzene, n-hexane, cyclohexane, methylene dichloride and o-dichlorobenzene.

This aspect of the process is carried out at a temperature in the range of from about 10° C. up to about 150° C. with a temperature range of 30°–120° C. being preferred. The reaction time is inversely proportional to the reaction temperature, with lower reaction temperatures giving rise to greater reaction times; and, accordingly, the reaction time ranges from about 30 minutes up to about 10 hours.

In this aspect of the process, the mole ratio of alcohol reactant to organic halide (e.g., allylic halide) is in the range of from 0.5:1.5 up to about 1.5:0.5 with a preferred ratio of alcohol to organic halide (e.g., allylic halide) being from about 1:1 up to about 1:1.2.

The mole ratio of base to alcohol in the reaction mass may be in the range of from about 0.75:1 up to about 1.5:1 with a preferred mole ratio of base:alcohol being from about 1:1 up to about 1.2:1.

The quantity of "phase transfer agent" in the reaction mass based on the amount of alcohol in the reaction mass may vary from 0.5 grams per mole of alcohol up to 25 grams of "phase transfer agent" per mole of alcohol with a preferred concentration of "phase transfer agent" being in the range of from about 2.5 up to about 7.5 grams of "phase transfer agent" per mole of alcohol.

This aspect of the process is preferably carried out at atmospheric pressure since that is the most convenient condition. However, lower or higher pressures can be used without detrimentally affecting the ultimate yield of desired product. The particular based used in the reaction is not critical, but, preferred are sodium hydroxide and potassium hydroxide.

The individual ethers which are reactants for our invention in the oxo process described, infra, can be obtained in pure form or in substantially pure form by conventional purification techniques. Thus, the products can be purified and/or islolated by distillation, extraction, crystallization, preparative chromatographic techniques and the like. It has been found desirable to purify the ethers by fractional distillation in vacuo.

The thus-formed ethers having the structure:

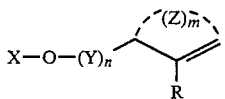

are then reacted with a mixture of carbon monoxide and hydrogen using a particular range of temperatures and partial pressures of hydrogen and carbon monoxide over one of several alternative "oxo" type reaction catalysts over a period of residence times.

Thus, the "oxo" reaction is carried out thusly:

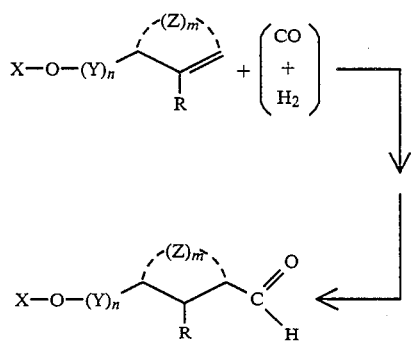

with the production of a small number of side products having the structure:

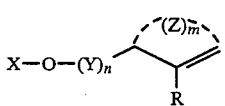

and an even smaller number of alcohols defined according to the structure:

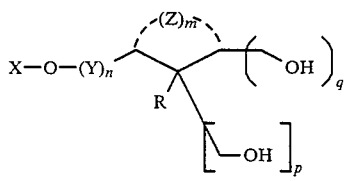

wherein X represents aryl, alkaryl, hydroxyalkyl, alkenyl, cycloalkenyl, lower alkyl or bicycloalkyl; wherein Y represents $C_1$-$C_3$ lower alkylene; wherein Z completes an alkyl substituted $C_6$ cycloalkyl ring or represents no moiety; wherein R represents hydrogen or methyl; wherein m represents 0 or 1; wherein n represents 0 or 1; wherein p represents 0 or 1 and wherein q represents 0 or 1 with the provisos that when m is 1, Z completes the alkyl substituted or unsubstituted $C_6$ cycloalkyl ring; that p is 1 when q is 0; and that when p is 0, q is 1. The reaction is carried out at temperature of between 150° C. and 300° C.; at pressures of between 20 and 250 atmospheres; with the ratio of partial pressure of carbon monoxide:hydrogen being from 0.1:1 up to 1:0.1. Any oxo type reaction catalyst may be used, but most preferably, the catalyst to yield the best perfume and flavor mixtures are as follows:

Dicobalt octacarbonyl;
Cobalt octanoate;
Palladium chloride;
Rhodium trichloride;
Iron pentacarbonyl;
Nickel tetracarbonyl;
Polymer-bonded rhodium catalyst (e.g., rhodium bonded on a polystyrene substrate);
Tris-triphenyl phosphine rhodium-1-chloride;
Rhodium Aceto acetate dicarbonyl;
Rhodium Aceto acetate/triphenyl phospine mixture.

The reaction time may vary from about 2 hours up to about 30 hours; and the reaction time is a function of the temperature and pressure of reaction; and the desired ratio of aldehyde:alcohol reaction product. Insofar as the instant invention is concerned, it is most desirable to have as high an aldehyde:alcohol ratio as possible causing the reaction condition to be extreme (high temperature, high pressure and long period of time) will create too high a ratio of alcohol:aldehyde reaction product. Accordingly, it is most advisable to stay within the limits set forth, supra.

At the end of the reaction, the reaction product is separated from the catalyst and unreacted materials by standard "work-up" means; e.g., neutralization of catalyst; followed by extraction and fractional distillation; usually an initial fractional distillation by means of distillation through a 3 or 4 plate or stone packed column; followed by a more careful fractionation of the bulked center-cut fractions on, for example, a spinning band column or multiplate (14–50 plate) fractionation column.

Examples of ether reactants which are useful in the practice of our invention and the resulting oxo reaction products and their organoleptic properties are as follows:

TABLE I

| Ether Reactant | Oxo Reaction Product | Perfumery Properties | Food Flavor Properties | Tobacco Flavor Properties |
|---|---|---|---|---|
| | | Diffusive, saw dust-like. | | |
| | | Green, spicy and calamus-like. | | |
| | | Natural pine, cypress and fir balsam. | | Adds body, woody, green, herbaceous and slight mouth coating on smoking with woody green and herbaceous aromas prior to smoking. |

TABLE I-continued

| Ether Reactant | Oxo Reaction Product | Perfumery Properties | Food Flavor Properties | Tobacco Flavor Properties |
| --- | --- | --- | --- | --- |
| (structure) | (structure) | Patchouli, coriander and woody with a chocolate topnote and dry cedarwood, and patchouli undertones. | | Adds body, woody, herbaceous, spicy and very aromatic on smoking in the main stream and the side stream; with woody, herbaceous and spicy aroma nuances prior to smoking. |
| (structure) | (structure) | Floral and ozoney with woody and fruity undertones. | | |
| (structure with OH) | (structure with OH) | Spicy (cinnamon), floral (carnation), herbaceous and fruity aroma with caryophyllene-like topnotes. | A bitter orange flavor. | |
| (structure) | (structure) | Citrus (grapefruit)-like aroma. | | |
| (structure with O—) | (structure with O—CH₃) | Green, floral (lilac) aroma. | A mango-like flavor. | |

When one or more the ether carboxaldehydes and reaction products containing same of our invention is used as a food flavor adjuvant, the nature of the co-ingredients included with said one or more ether carboxaldehydes in formulating the product composition will also serve to alter the organoleptic characteristics of the ultimate foodstuffs treated therewith. As used herein, in regard to flavors, the term "alter" in its various forms means "supplying or imparting flavor character or notes to otherwise bland relatively tasteless substance or augmenting the existing flavor characteristic where a natural flavor is deficient in some regard or supplementing the existing flavor impression to modify its quality, character or taste".

As used herein, the term "foodstuff" includes both solid and liquid ingestible materials which usually do but need not have nutritional value. Thus, foodstuffs include soups, convenience foods, beverages, dairy products, candies, fruits cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. According, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agaragar; carrageenan; cellulose and cellulose derivatives such as carboxymethyl cellulose and methyl cellulose; natural and synthetic gums such as gum arabic, gum tragacanth; gelatine; proteinaceous materials; lipids; carbohydrates; starches pectins, and emulsifiers, e.g., mono- and diglycerides of fatty acids, skim milk powder, hexose, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, turmeric and curcumin and the like; firming agents such as aluminum sodium sulfate, calcium chloride and calcium gluconate; texturizers; anti-caking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, butyric acid, caproic acid, caprylic acid, formic acid, 2-hexenoic acid, 3-hexenoic acid, isobutyric acid, isovaleric acid, propionic acid and valeric acid; ketones and aldehydes, e.g., acetaldehyde, acetone, acetyl methyl carbinol, acrolein, diacetyl, $\beta,\beta$-dimethylacrolein hexanal, 2-hexenal, cis-3-hexenal, 4(p-hydroxyphenyl)-2-butanone, $\alpha$-ionone, $\beta$-ionone, and 2-pentenal; alcohols, such as 1-butanol, trans-2-buten-1-ol, ethanol, gernaiol, 1-hexanol, cis-3-hexen-1-ol, 3-methyl-3-buten-1-ol, 1-pentanol, 1-penten-3-ol; esters, such as butyl acetate, ethyl acetate, ethyl butyrate, ethyl crotonate, ethyl propionate, 2-hexenyl acetate, 2-hexenyl butyrate, hexyl acetate, hexyl butyrate, isoamyl acetate, isopropyl butyrate, methyl butyrate, methyl caproate, methyl caprylate, propyl acetate, amyl acetate, amyl butyrate, benzyl salicylate, dimethyl anthranilate, ethyl methylphenylglycidate, ethyl succinate, isobutyl cinnamate, and terpenyl acetate; essential oils such as jasmine absolute, rose absolute, orris absolute, lemon essential oil and vanilla; lactones; sulfides, e.g., methyl sulfide and other materials such as maltol and citral as well as natural raspberry oil, orange oil, mango extract, pickled mango extract and natural cranberry juice concentrate, strawberry juice concentrate.

The specific flavoring adjuvants selected for use may be either solid or liquid, depending upon the desired physical form of the ultimate product, i.e., foodstuff, whether simulated or natural, and should, in any event, be capable or providing an environment in which the one or more ether carboxaldehydes of our invention can be disbursed or admixed to provide a homogeneous medium. In addition, selection of one or more adjuvants, as well as the quantities thereof, will depend upon the precise organoleptic raspberry character, strawberry character or plum character desired in the finished product. This, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of one or more ether carboxaldehydes of our invention employed in a particular instance can vary over a relatively wide range whereby its desired organoleptic effects (having reference to the nature of the product) are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for the purposes of enhancing the composition merely deficient in natural flavor or aroma. Thus, the primary requirements is that amount which is effective, i.e., sufficient to alter the organoleptic characteristics of the parent composition, whether foodstuff per se or flavoring composition. Thus, the use of insufficient quantities of one or more ether carboxaldehydes will, of course, substantially vitiate any possibility of obtaining the desired results while excess quantities prove needlessly costly and in extreme cases, may disrupt the flavor-aroma balance, thus proving self-defeating. Accordingly, the terminology "effect amount" and "sufficient amount" is to be accorded a significance in the context of the present invention consistent with the obtention of desired flavoring effects.

Thus and with respect to ultimate food compositions, it has been found that quantities of one or more ether carboxaldehydes ranging from a small but effective amount, e.g., 0.02 parts per million up to about 50 parts per million by weight based on total composition are suitable. Concentrations in excess of the maximum quantity stated are not normally recommended since they fail to provide commensurate enhancement of organoleptic properties. In those cases wherein the one or more ether carboxaldehydes is added to the foodstuff as an integral component of the flavoring composition, it is, of course, essential that the total quantity of flavoring composition employed be sufficient to yield an effective onr or more ether carboxaldehyde concentration in the foodstuff product.

The compositions described herein can be prepared according to conventional techniques well known as typified by cake batters and fruit juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing one or more ether carboxaldehyde with, for example, gum arabic, gum tragacanth, carrageenan and the like and thereafter spray-drying the resultant mixture whereby to obtain the particulate solid product. Prepared flavor mixes in powder form, e.g., a raspberry flavored powder are obtained by mixing dried solid, components, e.g., starch, sugar and the like and one more ether carboxaldehydes in a dry blender until the requisite degree of uniformity is achieved.

It is presently preferred to combine the one or more ether carboxaldehydes with the following adjuvants:
Parahydroxybenzyl acetone;
Vanillin;
Maltol;
$\alpha$-Ionone;
$\beta$-Ionone;
Isobutyl acetate;
Ethyl butyrate;
Dimethyl sulfide;
Acetic acid;
Acetaldehyde;
4-(2,6,6-trimethyl-1,3-cyclohexadien-1-yl)-2-butanone;
4-(6,6-dimethyl-2-methylene-3-cyclohexen-1-yl)-2-butanone;
2-(4-hydroxy-4-methylpentyl)norbornadiene produced according to Example I of U.S. Pat. No. 3,911,028;
$\beta$-Damascone(1-crotonyl-2,6,6-trimethylcyclohex-1-ene);
$\beta$-Damascenone(1-crotonyl-2,6,6-trimethylcyclohexa-1,3-diene);
Beta-cyclohomocitral(2,6,6-trimethylcyclohex-1-ene carboxaldehyde)
Isoamyl butyrate;
cis-3-hexenol-1;
Elemecine(4-allyl-1,2,6-trimethoxybenzene);
Isoelemecine(4-propenyl-1,2,6-trimethoxybenzene);
Cis-2-3-methyl pentenoic acid;
Ethyl-2-methyl-3-pentenoate;
Isobutyl-cis-2-methyl-3-pentenoate
2-Ethylidene-3-pentenal;
Orange oil;
Lemon oil;

Strawberry juice concentrate;
Cranberry juice concentrate;
Mango extract; and
Pickled mango extract.

One or more ether carboxaldehyde derivatives prepared in accordance with the process of our invention and one or more auxiliary perfume ingredients including, for example, alcohols other than those defined according to the structure:

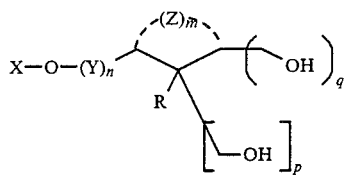

(wherein X represents aryl, alkaryl, hydroxyalkyl, alkenyl, cycloalkenyl, lower alkyl or bicycloalkyl; wherein Y represents $C_1$-$C_3$ lower alkylene; wherein Z completes an alkyl substituted $C_6$ cycloalkyl ring or represents no moiety; wherein R represents hydrogen or methyl; wherein m represents 0 or 1; wherein n represents 0 or 1; wherein p represents 0 or 1 and wherein q represents 0 or 1 with the provisos that when m is 1, Z completes the alkyl substituted or unsubstituted $C_6$ cycloalkyl ring; that p is 1 when q is 0; and that when p is 0, q is 1), aldehydes other than the ether carboxaldehydes of our invention defined according to the structure:

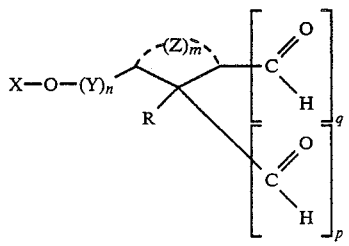

(wherein X represents aryl, alkaryl, hydroxyalkyl, alkenyl, cycloalkenyl, lower alkyl or bicycloalkyl; wherein Y represents $C_1$-$C_3$ lower alkylene; wherein Z completes an alkyl substituted $C_6$ cycloalkyl ring or represents no moiety; wherein R represents hydrogen or methyl; wherein m represents 0 or 1; wherein n represents 0 or 1; wherein p represents 0 or 1 and wherein q represents 0 or 1 with the provisos that when m is 1, Z completes the alkyl substituted or unsubstituted $C_6$ cycloalkyl ring; that p is 1 when q is 0; and that when p is 0, q is 1), ketones terpenic hydrocarbons, nitriles, esters, lactones, natural essential oils and synthetic essential oils may be admixed so that the combined odors of the individual components produce a pleasant and desired fragrance, particularly, and preferably, in pine, floral and lavender fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the over-all sensory effect of the perfume composition will be at least the sum total of the effects of each of the ingredients. Thus, one or more ether carboxaldehyde derivatives prepared in accordance with the process of our invention, can be used to alter, modify or enhance the aroma characteristics of a perfume composition, for example, by utilizing or moderating the olfactory reaction contributed by another ingredient in the composition.

The amount of one or more ether carboxaldehyde derivatives prepared in accordance with the process of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.01% of one or more ether carboxaldehyde derivatives prepared in accordance with the process of our invention and less than 50% of one or more ether carboxaldehyde derivatives prepared in accordance with the process of our invention or even less (e.g., 0.005%) can be used to impart a floral, lilac, carnation, green herbaceous, ozoney, fruity, citrus, grapefruits, spicy, cinnamon-like, woody, patchouli, coriander, natural pine-like, cypress, fir balsam-like, calamus-like and diffusive saw dust aroma nuances with caryophyllene-like and chocolate topnotes and fruity, woody, dry cedarwood and patchouli-like undertones to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

One or more ether carboxaldehyde derivatives prepared in accordance with the process of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produced from said perfumed polymers. When used as (an) olfactory component(s) as little as 0.2% of one or more ether carboxaldehydes derivatives prepared in accordance with the process of our invention will suffice to impart an intense floral, lilac, carnation, green, herbaceous, ozoney, fruity, citrus, grapefruit, spicy, cinnamon-like, woody, patchouli, coriander, natural pine-like, cypress, fir balsam-like, calamus-like, and diffuse saw dust aroma nuances with caryophyllene and chocolate topnotes and fruity, woody, dry cedarwood and patchouli-like undertones to lavender, floral or piney formulations. Generally, no more than 6% of one or more ether carboxaldehyde derivatives of our invention based on the ultimate end product is required in the perfumed article composition. Accordingly, the range of ether carboxaldehydes in the perfumed article is from about 0.2% by weight of the ether carboxaldehydes up to about 6% by weight based on the perfumed article. In addition, the perfume composition or fragrance composition of our invention can contain a vehicle or carrier for one or more ether carboxaldehyde derivatives prepared in accordance with the process of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g.) gum arabic, guar gum or xanthan gum) or components for encapsulating the composition (such as gelatin) as by coacervation; or such as a urea-formaldehyde polymer forming a capsule shell around a liquid perfumed center).

Our invention also relates to the utilization of controlled release technology for the controlled release of perfumes into gaseous environments from polymers such as mixtures of epsilon polycaprolactone polymers and polyethylene which poly epsilon caprolactone polymers are defined according to at leaste one of the structures:

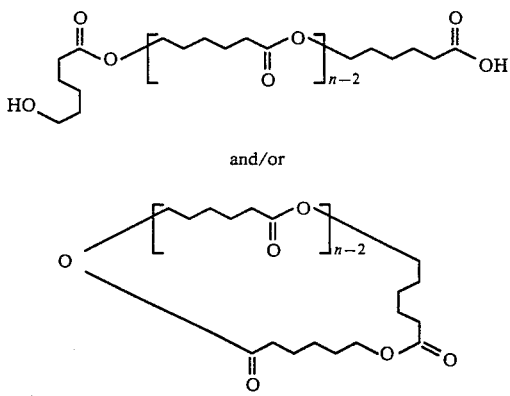

and/or wherein "n" is from about 50 up to about 1,200 with the proviso that the average "n" in the system varies from about 150 up to about 700 according to the mathematical statement:

$$[700 \geq \bar{n} \geq 150]$$

with the term $\bar{n}$ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$dM_t/dt = k_1 e^{-k_2 t}$$

wherein $k_1$ and $k_2$ are constants. According to Kydonieus, "Controlled Release Technologies: Methods, Theory, and Applications" (cited, supra), the amount of perfume composition released is proportional to time as long as the concentration of perfume material present, e.g., the ether carboxaldehydes of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the ether carboxaldehydes of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PCL-300 AND PCL-700". These polyepsilon caprolactone polymers are composed of a repeating sequence of non-polar methylene groups and relatively polar ester groups. The average number of repeating momomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such hydroquinone or compounds having the formula:

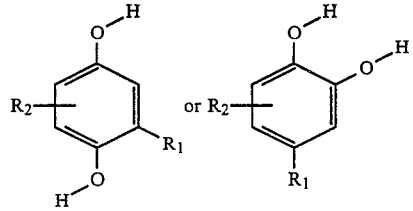

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix.

The method of incorporating the ether carboxaldehydes of our invention or perfume compositions containing same into the polymers may be according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylenepolyepsilon caprolactone polymer mixture (50:50) is mixed with one of the ether carboxaldehydes of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700: polyethylene in molten form is admixed with a high percentage of one of the ether carboxaldehydes of our invention and the mixture is solidified in the form of pellets or beads. These pellets or beads thus contain a high percentage of ether carboxaldehydes (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention at least one of the ether carboxaldehydes of our invention is added to the polymer in a large closed container or drum which is maintained under controlled temperature conditions while the polymer in a melted condition is mixed with at least one of the ether carboxaldehydes under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the ether carboxaldehydes of our invention is permitted to drip through the orifices onto a continuously moving, cooled conveyor upon which the polymer containing at least one of the ether carboxaldehydes of our invention solidifies into small size pellets with the perfume imprisoned therein. The apparatus useful in conjunction with this process advantageously includes a conveyor of a material which will not adhere to the polymer which contains at least one of ether carboxaldehydes of our invention.

In order that the droplets form into uniform pellets or beads, the conveyor is continuously washed with a liquid such as water to maintain the surface relatively cool. The pellets are delivered by the conveyor into a container and packaged for shipment.

Furthermore, one or more of the ether carboxaldehydes of our invention prepared in accordance with the process of our invention are capable of supplying and/or potentiating certain flavor and aroma notes usually lacking in many smoking tobacco flavors and substitute tobacco flavors heretofore provided.

As used herein in regard to smoking tobacco flavors, the terms "alter" and "modify" in their various forms means "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired woody, green, herbaceous and spicy aroma and taste nuances prior to and on smoking in both the main stream and in the side stream are created or enhanced and may be readily controlled and maintained at the desired uniform level regardless of variations in the tobacco components of the blend.

This invention further provides improved smoking tobacco additives and methods whereby various woody, green, herbaceous and spicy nuances are imparted (on smoking in the main stream and in the side stream) to smoking tobacco products and may be readily varied and controlled to produce the desired uniform flavor characteristics, particularly insofar as "oriental" like tobacco characteristics are concerned.

In carrying out this aspect of our invention, we add to smoking tobacco materials or a suitable substitute therefor (e.g., dried lettuce leaves) an aroma and flavor additive containing as an active ingredient at least one or more of the ether carboxaldehydes prepared according to the process of our invention.

In addition to one or more of the ether carboxaldehydes prepared in accordance to the process of our invention, other flavoring and aroma additives may be added to the smoking tobacco materials or substitute therefor either separately or in admixture with one or more of the ether carboxaldehydes of our invention as follows:

(i) Synthetic Materials

Beta-ethyl-cinnamaldehyde;
Beta-cyclohomocitral;
Eugenol;
Dipentene;
β-Damascenone;
β-Damascone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho[2,1b]furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed oil;
Coffee extract;
Bergamot oil;
Cocoa extract;
Nutmeg oil; and
Origanum oil.

An aroma and flavoring concentrate containing one or more of the ether carboxaldehyde prepared in accordance with the process of our invention and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or spicy notes, we have found that satisfactory results are obtained if the proportion by weight of the sum total of one or more ether carboxaldehydes is between 250 ppm and 1,500 ppm (0.025%–0.15%) of the active ingredients to the smoking tobacco material. We have further found that satisfactory results are obtained if the proportion by weight of the sum total of one or more ether carboxaldehydes of our invention is between 2,500 and 15,000 ppm (0.25%–1.50%).

Any convenient method for incorporation one or more of the ether carboxaldehydes prepared in accordance with the process of our invention in the tobacco product may be employed. Thus, one or more of the ether carboxaldehydes of our invention taken alone or along with other flavoring additives may be dissolved in a suitable solvent, such as ethanol, pentane, diethyl ether and/or other volatile organic solvents and the resulting solution may either be sprayed on the cured, cased and blended tobacco material or the tobacco material may be dipped into such solution. Under certain circumstances, a solution containing one or more of the ether carboxaldehydes of our invention taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the smoking tobacco or substitute therefor need be treated and the thus treated tobacco may be blended with other tobaccos before the ultimate tobacco product is formed. In such cases, the tobacco treated may have one or more of the ether carboxaldehydes of our invention in excess of the amounts or concentrations above-indicated so that when blended with other tobaccos, the final product will have the percentage within the indicated range.

In accordance with one specific example of our invention, an aged, cured and shredded domestic Burley tobacco is sprayed with a 20% ethyl alcohol solution of a 50:35:15 weight:weight:weight mixture of compounds containing materials having the following structures (in the order stated):

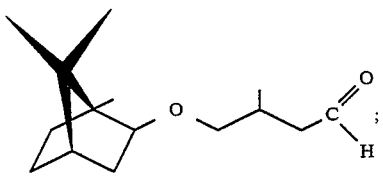

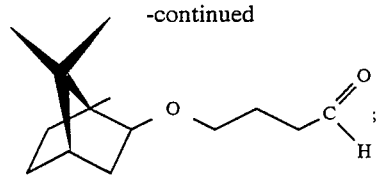

and

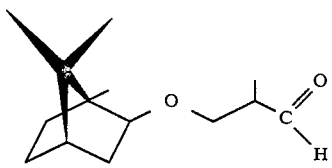

respectively in an amount to provide the tobacco composition containing 800 ppm by weight of the above-mentioned ether carboxaldehydes on a dry basis.

Thereafter, the alcohol is removed by evaporation and the tobacco is manufactured into cigarettes by the usual techniques. The cigarette when treated as indicated has a desired and pleasing aroma prior to smoking which can be described as woody, green, herbaceous and spicy and on smoking, in the main stream and in the side stream as spicy, oriental-like, Turkish tobacco-like, woody, green, with a slight mouth coating effect.

While our invention is particularly useful in manufacture of smoking tobacco, such as cigarette tobacco, cigar tobacco, and pipe tobacco, other smoking tobacco products formed from sheeted tobacco dust or fines may also be used. Likewise, one or more of the ether carboxaldehydes of our invention can be incorporated with materials such as filter tip materials, seam paste, packaging materials and the like which are used along with tobacco to form a product adapted for smoking. Furthermore, one or more of the ether carboxaldehydes of our invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following Examples I–VIII serve to illustrate processes for preparing the ether carboxaldehydes of our invention. The examples following Example VIII are illustrative of the organoleptic utilities of the ether carboxaldehydes of our invention. All parts and percentages given herein are by weight unless otherwise specified.

EXAMPLE I

Preparation of 4-(p-Cumenyloxy)Butyraldehyde

Reaction:

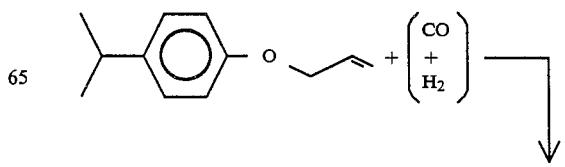

-continued

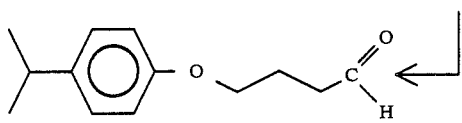

Into a 500 cc autoclave are placed the following materials:
176 grams (1 mole) of the ether having the structure:

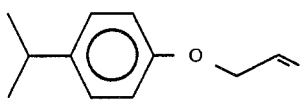

0.2 grams of rhodium carbonyl-di(triphenyl phosphine)-chloride
50 ml—Toluene

The autoclave is sealed and heated to 160° C. at a pressure of between 500 and 1,000 psig (using a 50:50 mole:mole mixture of carbon monoxide and hydrogen) and maintained at that pressure and temperature for a period of 12 hours.

At the end of the 12 hour period, the autoclave is cooled down and opened and the reaction mass is filtered. The resulting liquid is distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | /35 | /125 | 12:0 | 15.9 |
| 2 | 100 | 125 | 9:0 | 1.1 |
| 3 | 103 | 126 | 9:0 | 13.8 |
| 4 | 101 | 135 | 6:0 | 28.9 |
| 5 | 112 | 145 | 6:0 | 19.6 |
| 6 | 143 | 162 | 5:5 | 20.8 |
| 7 | 159 | 227 | 6:5 | 35.2 |

Fractions 2–6 are then bulked and redistilled on a spinning band column yielding the following fractions:

| Fraction No. | Vapor Temp. (°C.) | Liquid Temp. (°C.) | Vacuum mm/Hg. Pressure |
|---|---|---|---|
| 1 | /62 | /134 | 1:3 |
| 2 | 64 | 145 | 1:2 |
| 3 | 132 | 152 | 1:2 |
| 4 | 181 | 161 | 1:2 |
| 5 | 185 | 225 | 1:2 |

FIG. 1 is the GLC profile for the crude reaction product containing the compound having the structure:

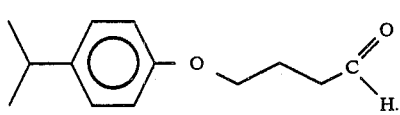

The peak indicated by reference numeral "10" on FIG. 1 is the peak for the compound having the structure:

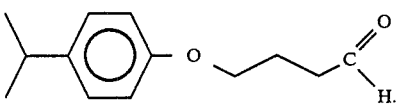

FIG. 2 is the NMR spectrum for the compound having the structure:

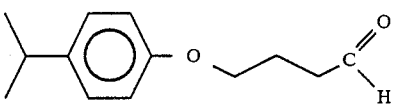

(conditions: Field strength 100 MHz; solvent: CFCl$_3$).

EXAMPLE II

Preparation of 4-(p-Cumenyloxy)-3-methylbutyraldehyde

Reaction:

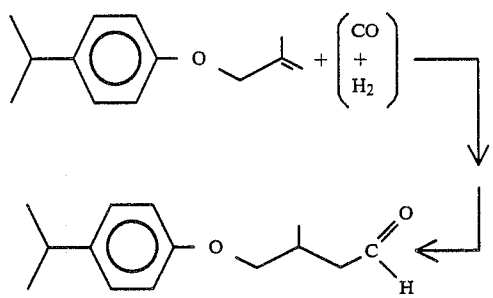

Into a 500 cc autoclave is placed:
200 grams of the compound having the structure:

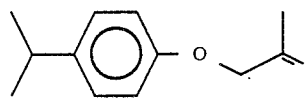

0.1 grams of Rhodium aceto acetate dicarbonyl.

The autoclave is sealed and pressurized to 1,000 psig at 120° C. using a 50:50 mole:mole mixture of carbon monoxide and hydrogen and maintained at that pressure and temperature for a period of 14.5 hours. GLC analysis indicates 83% product formed.

The reaction mass is cooled and the autoclave is opened. The contents are filtered and the liquid material is distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 97/103 | 133/140 | 3:5 | 18.3 |
| 2 | 104 | 140 | 3:0 | 27.8 |
| 3 | 134 | 158 | 2:4 | 47.1 |
| 4 | 140 | 180 | 4:0 | 39.5 |

Fractions 2, 3 and 4 are bulked and redistilled on a micro Vigreux column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 65/ | 142/ | | 2.9 |
| 2 | 75 | 145 | 3:4 | 3.2 |
| 3 | 73 | 148 | 3:4 | 3.0 |
| 4 | 70 | 150 | 3:4 | 2.3 |
| 5 | 98 | 155 | 3:4 | 7.6 |
| 6 | 95 | 157 | 3:4 | 7.6 |
| 7 | 80 | 164 | 3:6 | 11.5 |
| 8 | 94 | 172 | 3:6 | 1.5 |
| 9 | 104 | 193 | 3:6 | 3.1 |
| 10 | 100 | 200 | 3:6 | 5.7 |
| 11 | 80 | 220 | 3:6 | 3.2 |

FIG. 3 is the GLC profile for Fraction 4 of the foregoing distillation.

The peak indicated by reference numeral "30" is the peak for the compound having the structure:

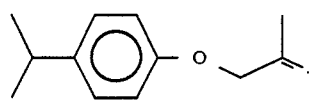

FIG. 4 is the NMR spectrum for the peak indicated by reference numeral "30" on FIG. 3 for the compound having the structure:

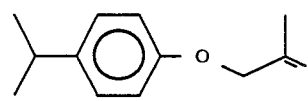

(Conditions: CFCl₃ solvent; Field strength: 100 MHz).

EXAMPLE III

Preparation of 4-(2-Bornyloxy)Butyraldehyde
Reaction:

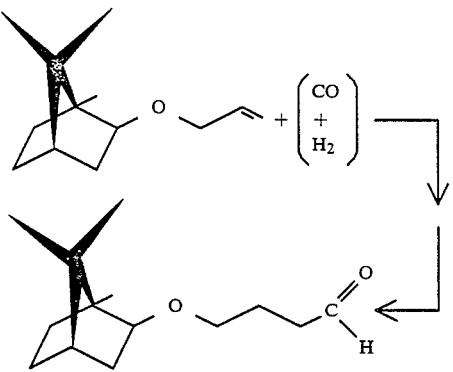

Into a 500 ml autoclave are placed the following ingredients:
Isobornyl allyl ether having the structure:

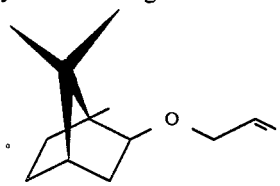

194 grams (1 mole)

Triphenylphosphine 2.0 grams
Rhodium Chloride-mono-carbonyltriphenylphosphine—0.2 grams
Toluene—50 ml The autoclave is sealed and pressurized to 500 psig using a 50:50 mole:mole mixture of carbon monoxide and hydrogen. The autoclave is heated to 200° C. and maintained at 500–700 psig for a period of 13 hours. At the end of the 13 hour period, the autoclave is cooled and opened yielding 462.9 grams of product (including toluene).

The reaction product is then distilled through a 12" Goodloe column yielding the following fractions:

| Fraction No. | Vapor Temp. (°C.) | Liquid Temp. (°C.) | Vacuum mm/Hg. Pressure | Wgt. of Fraction |
|---|---|---|---|---|
| 1 | 119/ | 165/ | 4:0 | 13.9 |
| 2 | 125 | 175 | 3:0 | 16.1 |
| 3 | 156 | 244 | 3:0 | 17.7 |
| 4 | 195 | 284 | 3:0 | 13.0 |

Fractions 2, 3 and 4 are bulked and redistilled through a spinning band column yielding the following fractions:

| Fraction No. | Vapor Temp. (°C.) | Liquid Temp. (°C.) | Vacuum mm/Hg. Pressure | Wgt. of Fraction |
|---|---|---|---|---|
| 1 | /94 | /134 | 2:8 | 9.7 |
| 2 | 95 | 140 | 2:6 | 8.7 |
| 3 | 62 | 147 | 2:6 | 3.5 |
| 4 | 102 | 163 | 2:4 | 2.8 |
| 5 | 114 | 178 | 2:4 | 3.3 |
| 6 | 70 | 194 | 2:8 | 5.9 |
| 7 | 64 | 240 | 2:9 | 4.4 |

The resulting product contains 70 percent by weight of the compound having the structure:

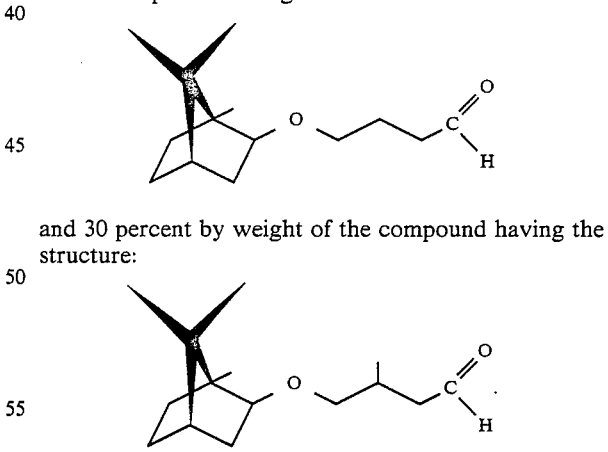

and 30 percent by weight of the compound having the structure:

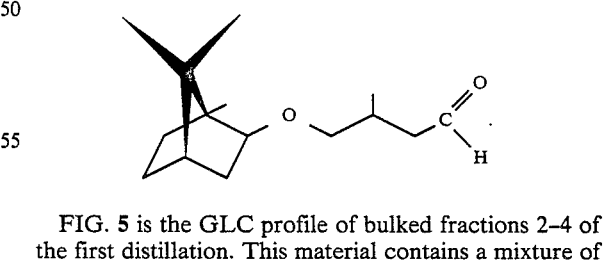

FIG. 5 is the GLC profile of bulked fractions 2–4 of the first distillation. This material contains a mixture of compounds having the structures:

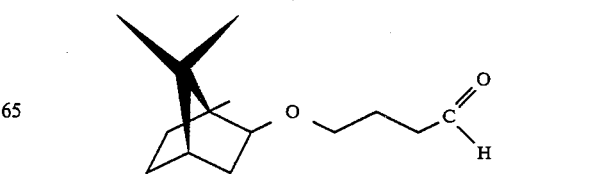

-continued
and

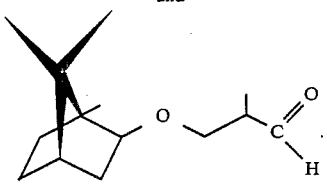

FIG. 6 is the GLC profile for fraction 5 of the spinning band distillation and contains the compounds having the structures:

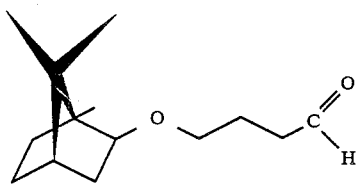

and

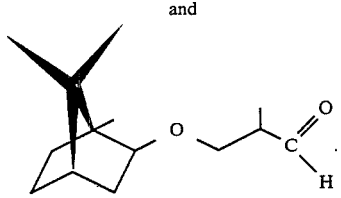

FIG. 7 is the NMR spectrum for the mixture of compounds containing 70 percent by weight of the compound having the structure:

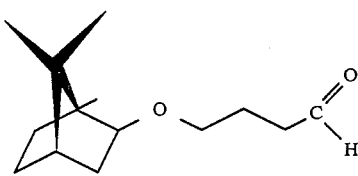

and 30 percent by weight of the compound having the structure:

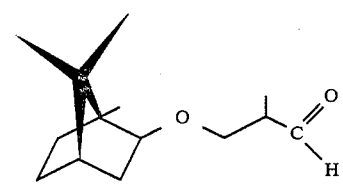

(conditions: CFCl₃ solvent; 100 MHz field strength).

EXAMPLE IV

Preparation of 3-Methyl-4-isobornyloxybutyraldehyde

Reaction:

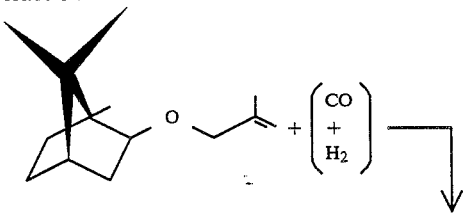

-continued

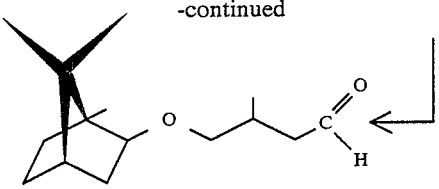

Into a 500 cc autoclave is placed the following materials:

(i) Isobornyl methallyl ether having the structure:

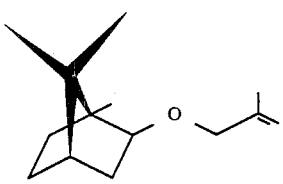

271 grams (77% pure);

(ii) Rhodium dicarbonyl acetoacetate 0.08 grams.

The autoclave is sealed, heated to 100°–140° C. and pressurized to 1,000 psig using a 50:50 (mole:mole) mixture of carbon monoxide and hydrogen and maintained at that pressure and temperature for a period of seven hours.

At the end of the seven hour period, the autoclave contents are cooled and the autoclave is opened and the contents are filtered.

The reaction mass is then distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 110/ | 135/ | 10:2 | — |
| 2 | 118 | 140 | 14:0 | 12.0 |
| 3 | 123 | 142 | 4:4 | 39.1 |
| 4 | 142 | 206 | 5:0 | 35.0 |
| 5 | 173 | 250 | 5:6 | 26.8 |

Fractions 3, 4 and 5 are bulked and redistilled on a spinning band distillation column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 80/ | 120/ | 1:5 | 12.5 |
| 2 | 68 | 125 | 1:5 | 7.7 |
| 3 | 68 | 139 | 1:4 | 6.0 |
| 4 | 95 | 137 | 1:3 | 8.9 |
| 5 | 95 | 146 | 1:3 | 9.0 |
| 6 | 96 | 141 | 1:3 | 9.0 |
| 7 | 98 | 143 | 1:4 | 8.5 |
| 8 | 99 | 145 | 1:4 | 10.0 |
| 9 | 100 | 152 | 2:0 | 10.5 |
| 10 | 102 | 166 | 1:4 | 10.1 |
| 11 | 100 | 195 | 1:5 | 8.9 |
| 12 | 104 | 225 | 1:5 | 6.9 |

FIG. 8 is the GLC profile for the crude reaction product of this example prior to the distillation containing the compound having the structure:

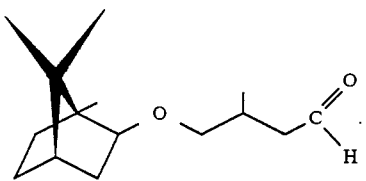

FIG. 9 is the GLC profile for fraction 6 of the spinning band distillation containing the compound having the structure:

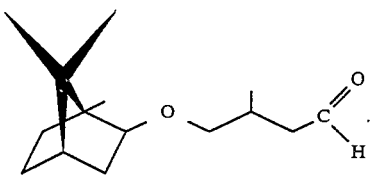

FIG. 10 is the NMR spectrum for fraction 6 of the spinning band distillation, for the compound having the structure:

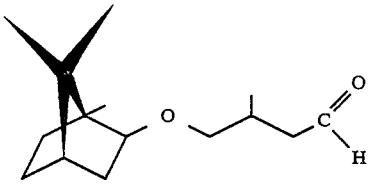

(Conditions: Solvent: CFCl$_3$; Field Strength: 100 MHz).

EXAMPLE V

Preparation of 4-(3,7-Dimethyl-6-octenyloxy)-3-methylbutyraldehyde

Reaction:

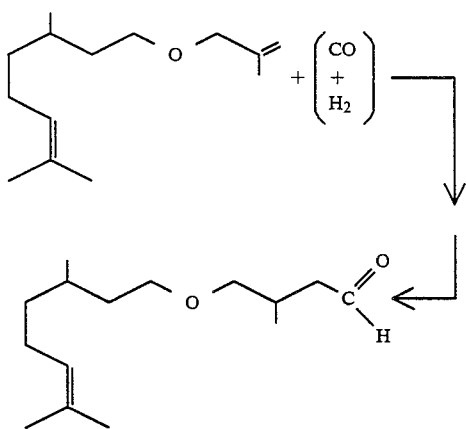

Into a 500 cc autoclave is placed the following materials:

(i) Citronellyl metallyl ether—305 grams (1.5 moles) (having the structure:

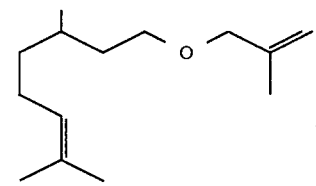

(ii) Triphenyl phosphine—4 grams (iii) Rhodium mono-carbonyl(triphenyl phosphine) chloride—0.4 grams (iv) Toluene—50 ml The autoclave is sealed and the contents heated to 140°-200° C. at a pressure of 1,000 psig using a 50:50 mole:mole ratio of carbon monoxide and hydrogen to pressurize same. The autoclave is maintained at that temperature and pressure for a period of seven hours. At the end of the seven hour period, the autoclave is cooled, opened and the contents filtered. The resulting period is distilled on a 2″ splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 29/39 | 52/104 | 1:7/1:7 | 28.1 |
| 2 | 104 | 130 | 2:5 | 12.2 |
| 3 | 138 | 153 | 1:4 | 30.2 |
| 4 | 155 | 170 | 2:2 | 39.2 |
| 5 | 150 | 65 | 8:0 | 22.5 |
| 6 | 135 | 176 | 4:8 | 46.8 |
| 7 | 148 | 205 | 4:8 | 29.2 |
| 8 | 140 | 221 | 4.0 | 5.6 |

Fractions 2-9 are then bulked and redistilled on a spinning band column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 46/54 | 124/117 | 1:3/1:3 | 2.3 |
| 2 | 64 | 117 | 1:2 | 5.0 |
| 3 | 68 | 118 | 1:2 | 5.9 |
| 4 | 69 | 130 | 1:2 | 7.9 |
| 5 | 70 | 132 | 1:2 | 9.6 |
| 6 | 72 | 133 | 1:2 | 8.5 |
| 7 | 73 | 138 | 1:2 | 9.0 |
| 8 | 78 | 140 | 1:2 | 10.4 |
| 9 | 88 | 141 | 1:2 | 9.4 |
| 10 | 98 | 136 | 1:1 | 5.7 |
| 11 | 100 | 137 | 1:1 | 6.0 |
| 12 | 100 | 138 | 1:1 | 11.7 |
| 13 | 102 | 138 | 1:1 | 8.1 |
| 14 | 102 | 142 | 1:1 | 10.1 |
| 15 | 102 | 142 | 1:1 | 10.3 |
| 16 | 107 | 144 | 1:1 | 10.8 |
| 17 | 102 | 146 | 1:1 | 9.1 |
| 18 | 66 | 146 | 1:1 | 5.7 |
| 19 | 104 | 171 | 1:0 | 7.1 |
| 20 | 96 | 196 | 1:1 | 7.4 |
| 21 | 60 | 220 | 1:0 | 2.8 |

FIG. 11 is the GLC profile for fraction 4 of the first distillation set forth above of the reaction product of this example containing the compound having the structure:

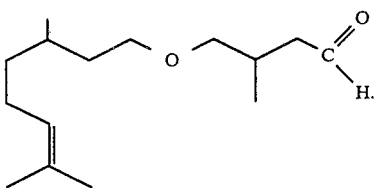

FIG. 12 is the GLC profile for fraction 19 of the final distillation and fraction 19 consists of the compound having the structure:

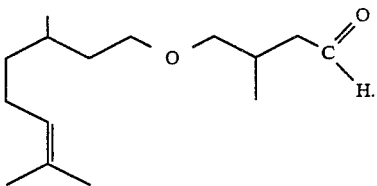

FIG. 13 is the NMR spectrum for fraction 19 of the second distillation (spinning band column distillation) and consists of the compound having the structure:

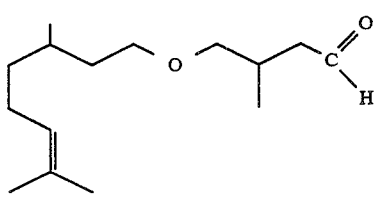

(conditions: Field strength: 100 MHz; solvent: $CFCl_3$).

EXAMPLE VI

Preparation of
4-Hydroxy-4-methyl-2-pentyloxy-butyraldehyde

Reaction:

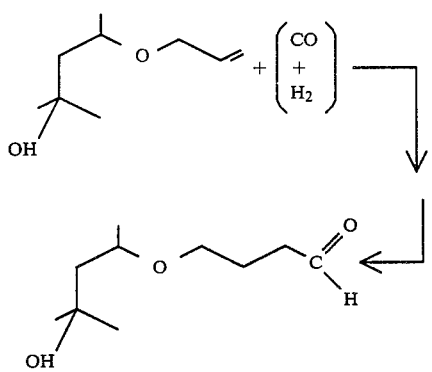

Into a 500 cc autoclave is placed the following materials:
(i) 4-allyloxy-2-methyl-2-pentanol (having the structure:

185 grams;
(ii) Rhodium-mono-carbonyl-di(triphenylphosphine)-chloride—0.2 grams
(iii) Triphenylphosphine—2 grams
(iv) Toluene—50 ml The autoclave is sealed and pressurized with a 50:50 mole:mole mixture of carbon monoxide and hydrogen to 500 psig and heated to 140° C. The temperature of 140° C. and pressure of 500 psig is maintained in the autoclave for a period of fourteen hours. At the end of the fourteen hour period, the autoclave is cooled and opened and the contents are filtered. The resulting product is then distilled on a spinning band column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 53/ | 98/ | 6:0 | 13.5 |
| 2 | 60 | 90 | 5:5 | 7.6 |
| 3 | 58 | 92 | 4:8 | 9.28 |
| 4 | 58 | 96 | 4:8 | 10.0 |
| 5 | 78 | 101 | 4:8 | 15.1 |
| 6 | 74 | 117 | 5:0 | 12.2 |
| 7 | 76 | 131 | 4:8 | 4.0 |
| 8 | 80 | 190 | 1:2 | 5.8 |
| 9 | 80 | 213 | 4:0 | 6.9 |
| 10 | 65 | 218 | 4:5 | 5.5 |

FIG. 14 is the GLC profile for the crude reaction product of this example.

FIG. 15 is the GLC profile for fraction 9 of the foregoing distillation.

FIG. 16 is the NMR spectrum for fraction 9 of the foregoing distillation (conditions: Solvent: $CFCl_3$; Field strength: 100 MHz).

EXAMPLE VII

Preparation of Terpinyloxybutanal

Reaction:

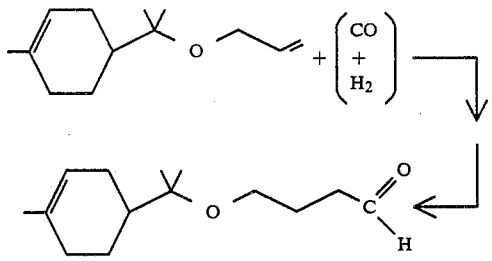

Into a 500 cc autoclave is placed the following ingredients:
(i) Terpinyl allyl ether (having the structure

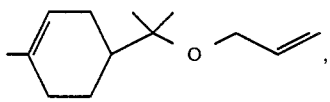

135 grams (ii) Rhodium chloride-mono-carbonyl-di(triphenyl-phosphene)—0.1 grams (iii) Triphenylphosphene—2 grams (iv) Toluene—50 ml The autoclave is sealed and pressurized to 500 psig using a 50:50 mole:mole mixture of carbon monoxide and hydrogen and the temperature of the autoclave is raised to 140° C. The autoclave is maintained at 500 psig and 140° C. for a period of twelve hours using the said carbon monoxide:hydrogen mixture.

At the end of the twelve hour period, the autoclave is cooled and the contents are removed and filtered. The resulting liquid is then distilled on a 1" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 32/ | 130/ | 8:0 | 14.5 |
| 2 | 120 | 150 | 14:0 | 9.0 |
| 3 | 138 | 162 | 13:0 | 18.9 |
| 4 | 110 | 155 | 7:0 | 28.2 |
| 5 | 149 | 172 | 12:0 | 27.9 |
| 6 | 157 | 290 | 12:0 | 13.8 |

Fractions 2–6 of this first distillation are bulked and redistilled on a spinning band column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 40/54 | 100/106 | 3:2 | 1.3 |
| 2 | 74 | 115 | 3:4 | 7.6 |
| 3 | 80 | 117 | 4:4 | 3.6 |
| 4 | 84 | 120 | 4:6 | 4.8 |
| 5 | 90 | 123 | 4:4 | 4.0 |
| 6 | 90 | 125 | 4:8 | 3.4 |
| 7 | 98 | 128 | 5:0 | 4.2 |
| 8 | 84 | 135 | 5:0 | 4.4 |
| 9 | 110 | 142 | 5:0 | 5.6 |
| 10 | 110 | 145 | 5.0 | 6.3 |
| 11 | 110 | 154 | 5:0 | 6.9 |
| 12 | 110 | 180 | 4:8 | 4.7 |

FIG. 17 is the GLC profile for the crude reaction product prior to distillation containing the compound having the structure:

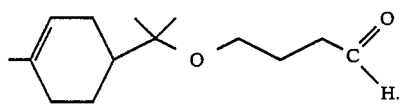

FIG. 18 is the GLC profile for fraction 11 of the foregoing distillation containing the compound having the structure:

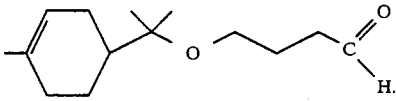

The peak indicated by reference numeral "180" on the GLC profile of FIG. 18 is the peak for the compound having the structure:

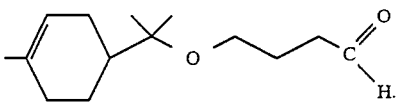

FIG. 19 is the NMR spectrum for peak 180 of FIG. 18 (Fraction 11 of the foregoing distillation) which is the peak for the compound having the structure:

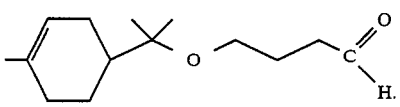

EXAMPLE VIII

Preparation of 8-Methoxy-p-methane-2-carboxaldehyde

Reaction:

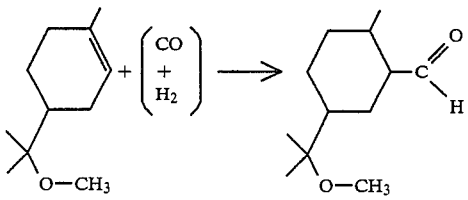

Into a 1000 cc autoclave is placed the following ingredients:

(i) "Orange flower ether" (having the structure:

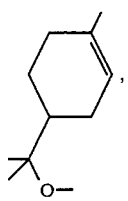

501 grams (3 moles);

(ii) Rhodium acetoacetate-dicarbonyl—0.1 grams

The autoclave is sealed and pressurized to 1,000 psig using a 50:50 mole:mole mixture of carbon monoxide and hydrogen and heated to a temperature of 160° C. The autoclave contents are maintained at 1,000 psig and 60° C. for a period of seven hours.

At the end of the seven hour period, the autoclave contents are cooled, the autoclave is opened and the contents are removed and filtered. The resulting liquid filtrate is then distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 82/ | 102/ | 10 |
| 2 | 93 | 113 | 18 |
| 3 | 98 | 118 | 17 |
| 4 | 114 | 128 | 14 |
| 5 | 132 | 142 | 13 |
| 6 | 142 | 151 | 9 |
| 7 | 143 | 160 | 6 |
| 8 | 168 | 220 | 6 |

Fractions 5–7 of this distillation product are bulked and redistilled on a spinning band column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 50/59 | 102/ | 9:3 | 4.3 |
| 2 | 70 | 120 | 8:7 | 13.7 |
| 3 | 87 | 116 | 5:4 | 11.6 |
| 4 | 84 | 117 | 2:5 | 20.0 |
| 5 | 84 | 116 | 2:5 | 17.4 |
| 6 | 84 | 116 | 2:5 | 15.9 |
| 7 | 90 | 103 | 2:6 | 10.7 |
| 8 | 91 | 125 | 2:6 | 17.4 |
| 9 | 94 | 127 | 2:6 | 35.2 |
| 10 | 108 | 134 | 2:8 | 32.0 |
| 11 | 120 | 161 | 2:8 | 31.9 |
| 12 | 43 | 200 | 2:8 | 4.1 |

FIG. 20 is the GLC profile for the crude reaction product of this example containing the compound having the structure:

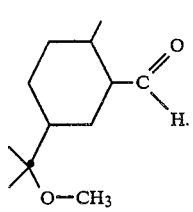

FIG. 21 is the GLC profile of fraction 8 of the foregoing spinning band distillation containing the compound having the structure:

FIG. 22 is the NMR spectrum for the compound having the structure:

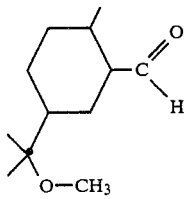

(Conditions: Field strength: 100 MHz; solvent: CFCl₃).

EXAMPLE IX

Pine Fragrance

The following pine fragrance formulations are prepared:

| Ingredients | Parts By Weight | | |
|---|---|---|---|
| | IX-A | IX-B | IX-C |
| Isobornyl acetate | 100 | 100 | 100 |
| Camphor | 10 | 10 | 10 |
| Terpineol | 25 | 25 | 25 |
| Fir balsam absolute (50% in diethyl phthalate) | 20 | 20 | 20 |
| Coumarin | 4 | 4 | 4 |
| Linalool | 30 | 30 | 30 |
| Frenchyl alcohol | 10 | 10 | 10 |
| Anethol | 12 | 12 | 12 |
| Lemon terpenes washed | 50 | 50 | 50 |
| Borneol | 5 | 5 | 5 |
| Galbanum oil | 5 | 5 | 5 |
| Turpentine Russian | 150 | 150 | 150 |
| Eucalyptol | 50 | 50 | 50 |
| 2,2,6-trimethyl-1-cyclohexene-1-carboxaldehyde | 12 | 12 | 12 |
| Maltol (1% in diethyl phthalate) | 5 | 5 | 5 |
| Compound having the structure: | 28 | 0 | 0 | prepared according to Example I

Compound having the structure: 0 28 0 prepared according to Example III

Compound having the structure: 0 0 28 prepared according to Example IV

The compound having the structure:

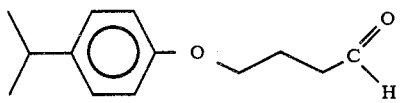

imparts to the pine formulation an intense diffusive saw dust nuance. Accordingly, the pine formulation can be described as "piney with an intense saw dust-like undertone".

The compound having the structure:

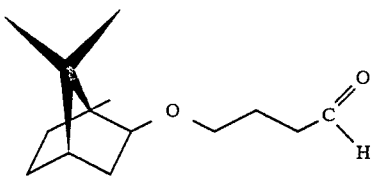

imparts to this piney formulation a very natural-like cypress, fir balsam-like aroma with lavender spiked topnotes. Accordingly, the formulation this prepared can be described as "natural piney with cypress-like and fir balsam undertones and lavender spiked topnotes"

The compound having the structure:

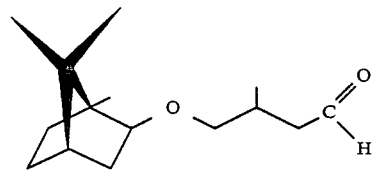

imparts to this piney formulation a patchouli, coriander, mahogany-wood-like character. Accordingly, the formulation can be described from a perfumery standpoint as "piney with patchouli, coriander and mahogany-like and dry cedarwood undertones with faint chocolate topnotes".

EXAMPLE X

Floral Perfume Compositions

The compound having the structure:

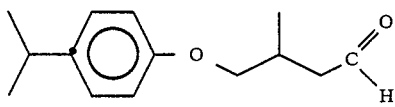

produced according to Example II has a green, spicy, calamus-like aroma. This material has great warmth and richness and blends well many floral concepts. It is a rather unique floral note of great value to perfumery. Its use may be demonstrated by the following floral fragrance whereby the compound having the structure:

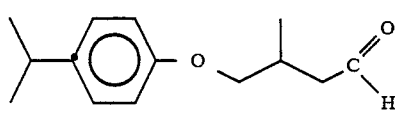

is used to the extent of 5% by weight.

The compound having the structure:

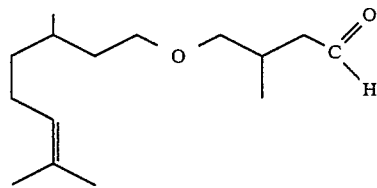

produced according to Example V imparts to this floral fragrance a very "ozoney" nuance causing it to be quite useful in the "fresh air dried-cloves aroma" type fragrance. The addition of 5 percent by weight of the compound having the structure:

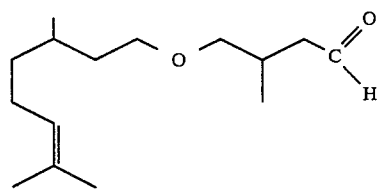

imparts a very desirable fresh air character.

The compound having the structure:

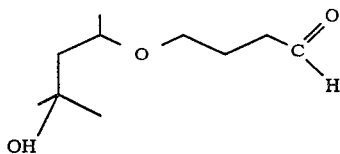

imparts to the floral formulation a spicy (cinnamon), carnation-like, herbaceous and fruity undertone.

All four of these products perform quite well in fragrances and are judged to be very valuable fragrance materials:

| | FLORAL FRAGRANCE | | | |
|---|---|---|---|---|
| | "A" | "B" | "C" | "D" |
| Citronellol | 12.3 | 12.3 | 12.3 | 5.0 |
| Geraniol | 2.5 | 2.5 | 2.5 | 5.0 |
| Amyl Cinnamic Aldehyde | 24.6 | 24.6 | 24.6 | 5.0 |
| Galaxolide ® 50 (Trademark Tricyclic Isochroman of International Flavors & Fragrances Inc.) | 9.8 | 9.8 | 9.8 | 5.0 |
| Vertenex High Cis (Cis-t Butylcyclohexenyl Acetate; Para Isomer) | 7.4 | 7.4 | 7.4 | 5.0 |
| Rose Oxide | 0.7 | 0.7 | 0.7 | 5.0 |
| Cinnamic Alcohol | 19.6 | 19.6 | 19.6 | 5.0 |
| Aldehyde C-11 (n-Undecylenic Aldehyde) | 0.5 | 0.5 | 0.5 | 5.0 |
| Aldehyde C-12 (n-Dodecyl Aldehyde in 10% solution in diethyl phthalate) | 0.5 | 0.5 | 0.5 | 5.0 |
| Citronellal (10% solution in diethyl phthalate) | 0.5 | 0.5 | 0.5 | 5.0 |
| Phenyl Ethyl Acetate | 2.5 | 2.5 | 2.5 | 5.0 |
| Ylang oil | 1.2 | 1.2 | 1.2 | 5.0 |
| Indisan (Hydrogenated derivative of reaction product of Camphene and Resorcinol) | 3.7 | 3.7 | 3.7 | 5.0 |
| Musk Ketone | 5.0 | 5.0 | 5.0 | 5.0 |
| Oakmoss Resin | 0.5 | 0.5 | 0.5 | 5.0 |
| Liatrix Absolute (10% in diethyl phthalate) | 2.5 | 2.5 | 2.5 | 5.0 |
| Vetiver Acetate | 1.2 | 1.2 | 1.2 | 5.0 |

-continued

| FLORAL FRAGRANCE | | | | |
|---|---|---|---|---|
| | "A" | "B" | "C" | "D" |
| Diethyl Phthalate | 5.0 | 5.0 | 5.0 | 5.0 |
| Compound having the structure: | 5.0 | 0 | 0 | 0 |

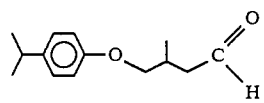

produced according to Examples II.

| Compound having the structure: | 0 | 5.0 | 0 | 0 |
|---|---|---|---|---|

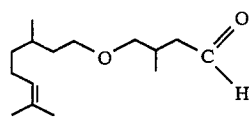

produced according to Example V.

| Compound having the structure: | 0 | 0 | 5.0 | 0 |
|---|---|---|---|---|

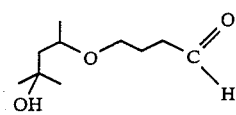

produced according to Example VI.

| Compound having the structure: | 0 | 0 | 0 | 5.0 |
|---|---|---|---|---|

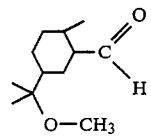

produced according to Example VIII.

The compound having the structure:

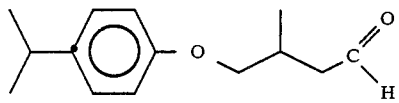

imparts to this floral fragrance green, spicy and calamus-like aroma nuances. Accordingly, the fragrance can be described as "floral with green, spicy and calamus-like undertones".

The compound having the structure:

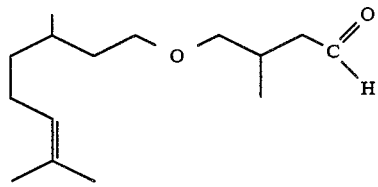

imparts to this floral formulation a very ozoney type nuance. Accordingly, the fragrance thus produced can be described as "floral with ozoney and fresh air dried cloth undertones".

The compound having the structure:

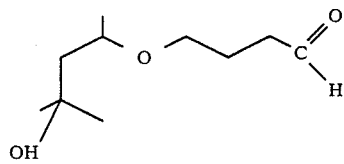

imparts to this floral formulation a cinnamon-like, carnation-like, herbaceous and fruity aroma profile. Accordingly, the fragrance can be described as "floral with spicy (cinnamon), carnation-like, herbaceous and fruity undertones".

The compound having the structure:

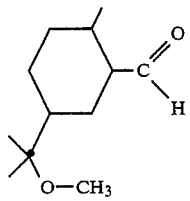

imparts to this floral formulation an intense lilac and green undertone. Accordingly, the fragrance can be described as "floral with lilac and green undertones".

EXAMPLE XI

Preparation of Lilac Fragrance

The following mixture is prepared:

| Hydroxycitronellal | 22% |
|---|---|
| Phenyl Ethyl Alcohol | 12% |
| Heliotropine | 12% |
| Linalcol | 8% |
| Cinnamic Alcohol | 4% |
| Indole - 10% in Diethyl Phthalate | 2% |
| Benzyl Acetate | 8% |
| Anisic Alcohol | 8% |
| Coumarin - 10% in Diethyl Phthalate | 4% |
| Compound having the structure: | 4% |

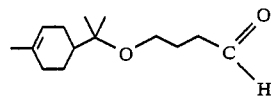

The compound having the structure:

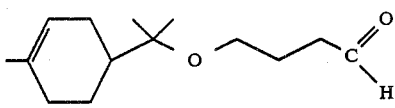

imparts to this lilac fragrance an interesting citrusy (grapefruit-like) undertone. According the fragrance can be described as "lilac with a citrusy, grapefruit-like undertone".

EXAMPLE XII

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| SUBSTANCE | AROMA DESCRIPTION |
|---|---|
| 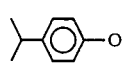 | Diffusive, saw dust-like. |
| 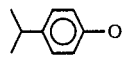 | Green, spicy and calamus-like. |
|  | Natural pine, cypress and fir balsam. |
| 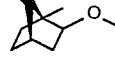 | Patchouli, coriander and woody with a chocolate topnote and dry cedarwood and patchouli undertones. |
| 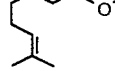 | Floral and ozoney with woody and fruity undertones. |
| 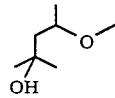 | Spicy (cinnamon), floral (carnation), herbaceous and fruity aroma with caryophyllene-like topnotes. |
| 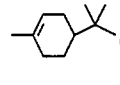 | Citrus (grapefruit)-like aroma. |
| 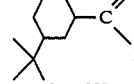 | Green, floral (lilac) aroma. |
| Fragrance prepared according to Example IX(A). | Piney with an intense saw dust-like undertone. |
| Fragrance prepared according to Example IX(B). | Natural piney with cypress-like and fir balsam undertones and lavender spike topnotes. |
| Fragrance prepared according to Example IX(C). | Piney with patchouli, coriander and mahogany-like and dry cedarwood undertones with faint chocolate topnotes. |
| Fragrance prepared according to Example X(A). | Floral with green, spicy and calamus-like undertones. |
| Fragrance prepared according to Example X(B). | Floral with ozoney and fresh air dried cloth undertones. |
| Fragrance prepared according to Example X(C). | Floral with spicy (cinnamon), carnation-like, herbaceous and fruity undertones. |
| Fragrance prepared according to Example X(D). | Floral with lilac and green undertones. |
| Fragrance prepared according to Example XI. | Lilac with a citrusy, grapefruit-like undertone. |

EXAMPLE XIII

Perfumed Liquid Detergents

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table II of Example XII are prepared containing 0.10%, 0.15%, 0.20%, 0.25%, 0.30% and 0.35% of the substance set forth in Table II of Example XII. They are prepared by adding and homogeneously mixing the appropriate quantity of substance set forth in Table II of Example XII in the liquid detergent. The detergents all possess excellent aromas as set forth in Table II of Example XII, the intensity increasing with greater concentrations of substance as set forth in Table II of Example XII.

EXAMPLE XIV

Preparation of Colognes and Handkerchief Perfumes

Compositions as set forth in Table II of Example XII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XII are imparted to the colognes and to the handkerchief perfumes at all levels indicated.

EXAMPLE XV

Preparation of Soap Compositions

One hundred grams of soap chips (per sample) (IVORY ®, produced by the Procter & Gamble Company of Cincinnati, Ohio), are each mixed with one gram samples of substances as set forth in Table II of Example XII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example XII.

EXAMPLE XVI

Preparation of Solid Detergent Compositions

Detergents are prepared using the following ingredients according to Example I of Canadian Patent No. 1,007,948 (incorporated herein by reference):

| Ingredient | Percent by Weight |
|---|---|
| Neodol ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table II of Example XII. Each of the detergent samples has an excellent aroma as indicated in Table II of Example XII.

EXAMPLE XVII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table II of Example XII.

Fabric softening compositions prepared according to Example I at column 15 of U.S. Pat. No. 3,632,396 having aroma characteristics as set forth in Table II of Example XII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example XII, supra.

EXAMPLE XVIII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

|  | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example XII, supra | 0.10 |

The perfume substances as set forth in Table II of Example XII add aroma characteristics as set forth in Table II of Example XII which are rather intense and aesthetically pleasing to the users of the soft-feel, good-hold pump hair sprays.

EXAMPLE XIX

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 wt ratio of A:B and cooled to 45° C. and 0.3 wt percent of perfuming substance as set forth in Table II of Example XII is added to the mixture. The resulting mixture is cooled to 40° C. and blending is carried out for an additional one hour in each case. At the end of this blending period, the resulting material has a pleasant fragrance as indicated in Table II of Example XII.

EXAMPLE XX

Tobacco Formulation

A tobacco mixture is prepared by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1000 ppm of the compound having the structure:

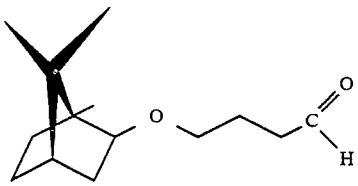

produced according to Example III. The control cigarettes not containing the compound having the structure:

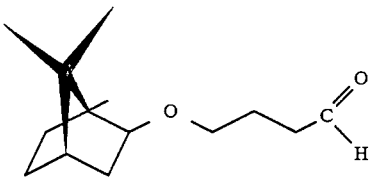

and the experimental cigarettes which contain the compound having the structure:

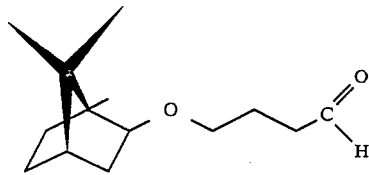

are evaluated by paired comparison and the results are as follows:

The experimental cigarettes are found to have a woody, green and herbaceous aroma prior to smoking and are found to have body and a slight mouth coating with woody, green and herbaceous nuances on smoking in both the main stream and the side stream. The experimental cigarettes are found to be sweeter and more aromatic on smoking in the main stream and the side stream. All cigarettes are evaluated for smoke flavor with a 20 mm cellulose acetate filter.

When used in the filter rather than on the tobacco the cigarettes having in the filter the compound having the structure:

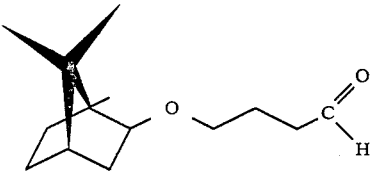

have a sweet, woody, green, herbaceous flavor and taste prior to and on smoking.

EXAMPLE XXI

Tobacco Formulation

A tobacco mixture is prepared by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |

-continued

| Ingredients | Parts by Weight |
| --- | --- |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1000 ppm of the compound having the structure:

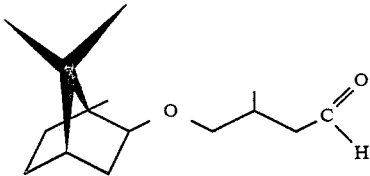

produced according to Example IV. The control cigarettes not containing the compound having the structure:

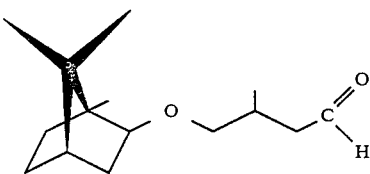

and the experimental cigarettes which contain the compound having the structure:

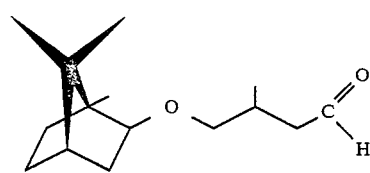

are evaluated by paired comparison and the results are as follows:

The experimental cigarettes are found to have woody, herbaceous and spicy aroma nuances prior to smoking and have body and added aromaticity with woody, herbaceous and oriental-like, spicy nuances on smoking in both the main stream and the side stream. All cigarettes are evaluated for smoke flavor with a 20 mm cellulose acetate filter.

When used in the filter rather than on the tobacco the cigarettes having in the filter the compound having the structure:

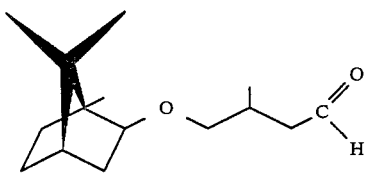

have an aromatic, woody, herbaceous, spicy aroma and taste both prior to and on smoking.

EXAMPLE XXII

Each of the fragrance materials of Table II of Example XII, supra, are added to a 50:50 weight:weight mixture of low density polyethylene:polyepsilon caprolactone PCL-700 forming pellets with scents as set forth in Table II of Example XII, supra.

75 Pounds of a 50:50 mixture of PCL-700 polyepsilon caprolactone (manufactured by the Union Carbide Corporation of New York, N.Y. having a melting point of about 180°–190° F.): Low density polyethylene, are heated to about 250° F. in a container of the kind illustrated in FIGS. 23 and 24. 25 Pounds of each of the fragrance materials as set forth in Table II of Example XII, is then quickly added to the liquified polymer mixture, the lid 228 is put in place and agitating means 273 are actuated. The temperature is then raised to about 260° F. and the mixing is continued for 5–15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table II of Example XII, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example XII, supra. The sheets of films are cut into strips of 0.25" in width×3" in length and placed intro room air fresheners.

On operation of the room air freshener, after four minutes, the room in each case has an aesthetically pleasing aroma with no foul odor being present, the aroma being described in Table II of Example XII, supra.

EXAMPLE XXIII

Flavor Formulation

The following natural orange formulation is prepared:

| Ingredients | Parts by Weight |
| --- | --- |
| Compound defined according to the structure:<br/>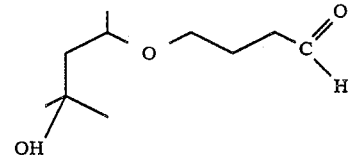 | 26.0 |

| Ingredients | Parts by Weight |
| --- | --- |
| prepared according to Example VI. | |
| Natural Lemon Oil Terpeneless | 10.0 |
| Acetaldehyde | 0.6 |
| Alpha-terpineol | 2.1 |
| Citral | 1.8 |
| Carvone | 0.24 |
| Terpinolene | 1.2 |
| alpha-terpinene | 0.25 |
| Diphenyl | 0.25 |
| Alpha Fenchyl Alcohol | 0.25 |
| Limonene | 0.35 |
| Linalool | 0.25 |
| Geranyl Acetate | 0.25 |
| Nootkatone | 0.25 |
| Neryl Acetate | 0.25 |

The second flavor formulation is prepared which is identical to the above formulation, except without the compound having the structure:

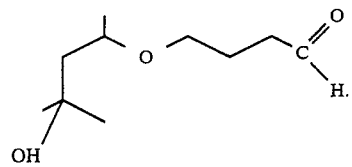

The flavor formulation with the compound having the structure:

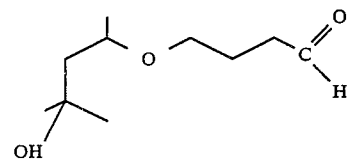

has a definite "natural orange" aroma due to the addition of bitter orange principals to this citrus flavor.

The citrus flavor with the compound having the structure:

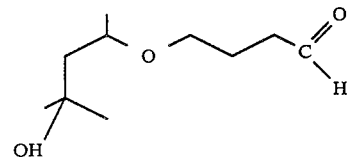

is used in the following examples.

EXAMPLE XXIV

A. Powder Flavor Composition

20 Grams of the flavor composition of Example XXIII containing the compound having the structure:

is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavor

The following mixture is prepared:

| Ingredients | Parts by Weight |
|---|---|
| Liquid Citrus Flavor Composition of Example XXIII | 20.0 |
| Propylene glycol | 9.0 |
| Cab-O-Sil ® M-5 (Brand of Silica produced by the Cabot Corporation of 125 High Street, Boston, Massachusetts 02110: Physical Properties: Surface area: 200 m$^2$/gm Nominal particle size: 0.012 microns Density: 2.3 lbs/cu. ft. | 5.00 |

The Cab-O-Sil is dispersed in the liquid citrus flavor compositions of Example XXIII with vigorous stirring, thereby resulting in a viscous liquid. 71 Parts by weight of the powder flavor composition of Part "A", supra, is then blended into the said viscous liquid, with stirring, at 25° C. for a period of 30 minutes resulting in a dry, free flowing sustained release flavor powder.

EXAMPLE XXV

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XXIII is added to the solution which is then homogenized to form an emulsion having particle size typically in the range of 5-40 microns. This material is kept at 120° F. under which conditions the gelatin will not jell.

Coacervation is induced by adding, slowly and uniformly 40 parts by weight of a 20% aqueous solution of sodium sulphate. During coacervation the gelatin molecules are deposited uniformly about each oil droplet as a nucleus.

Gelatin is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXVI

Chewing Gum

100 Parts by weight of chicle are mixed with 4 parts by weight of the flavor prepared in accordance with Example XXIV(B). 300 Parts of sucrose and 100 parts of corn syrup are added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long lasting citrus flavor.

EXAMPLE XXVII

Chewing Gum

100 Parts by weight of chicle are mixed with 18 parts by weight of the flavor prepared in accordance with Example XXV. 300 Parts of sucrose and 100 parts of corn syrup are then added. Mixing is effected in a ribbon blender with jacketed side walls of the type manufacuted by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long lasting citrus flavor.

EXAMPLE XXVIII

Toothpaste Formulation

The following separate groups of ingredients are prepared:

| Parts by Weight | Ingredients |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluroide |
| Group "B" | |
| 12.500 | Calcium Carbonate |
| 37.200 | Dicalsium Phosphate (Dihydrate) |
| Group "C" | |
| 2.000 | Sodium N—Lauroyl Sarcosinate (foaming agent) |
| Group "D" | |
| 1.200 | Flavor Materials of Example XXIV(B) |

Procedure:
1. The ingredients in Group "A" are stirred and heated in a steam jacketed kettle to 160° F.;
2. Stirring is continuted for an additional three to five minutes to form a homogeneous gel;
3. The powders of Group "B" are added to the gel, while mixing, until a homogeneous paste is formed;
4. With stirring, the flavor of "D" is added and lastly the sodium n-lauroyl sarcosinate;
5. The resultant slurry is then blended for one hour. The completed paste is then transferred to a three roller mill and then homogenized, and finally tubed.

The resulting toothpaste when used in a normal toothbrushing procedure yields a pleasant citrus flavor, of constant strong intensity throughout said procedure (1-1.5 minutes).

EXAMPLE XXIX

Chewable Vitamin Tablets

The flavor material produced according to the process of Example XXIV(B) is added to a Chewable Vitamin Tablet Formulation at a rate of 10 gm/Kg which chewable vitamin tablet formulation is prepared as follows:

In a Hobart Mixer the following materials are blended to homogeneity:

|  | Gms/1000 tablets |
| --- | --- |
| Vitamin C (ascorbic acid) as ascorbic acid-sodium ascorbate mixture 1:1 | 70.00 |
| Vitamin B₁ (thiamine mononitrate) as Rocoat ® thiamine mononitrate 33⅓% (Hoffman La Roche) | 4.0 |
| Vitamin B₂ (riboflavin) as Rocoat ® riboflavin 33⅓% | 5.0 |
| Vitamin B₆ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B₁₂ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XXIV(B) | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A Acetate and 0.6 g Vitamin D are then added as beadlets. The entire blend is then compressed using concave punches at 0.5 g each.

Chewing of the resultant tablets yields a pleasant, long-lasting, consistenly strong citrus flavor for a period of 12 minutes.

EXAMPLE XXX

Chewing Tobacco

Onto 100 pounds of tobacco for chewing (85% Wisconsin leaf and 15% Pennsylvania leaf) the following casing is sprayed at a rate of 30%:

| Ingredients | Parts by Weight |
| --- | --- |
| Corn Syrup | 60.0 |
| Licorice | 10.0 |
| Glycerine | 20.0 |
| Fig Juice | 4.6 |
| Prune Juice | 5.0 |
| Flavor Material of Example XXIV(B) | 0.4 |

The resultant product is redried to a moisture content of 20%. On chewing, this tobacco has an excellent substantially consistent, long-lasting citrus and licorice aroma and taste profile in conjunction with the tobacco note.

EXAMPLE XXXI

To 100 parts by weight of goya ® mango nectar (produced by the Goya Corporation of New York, N.Y.) is added 10 ppm of the compound having the structure:

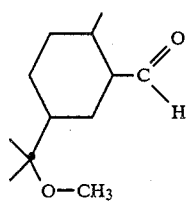

prepared according to Example VIII. The compound having the structure:

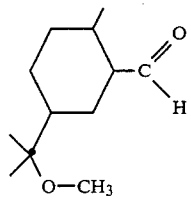

adds to the mango nectar a very natural nuance which although present in natural mango is lost in the canning process when mango nectar is prepared and canned in the usual manner.

The ether carboxaldehydes of our invention are indicated, for example, as having structures such as:

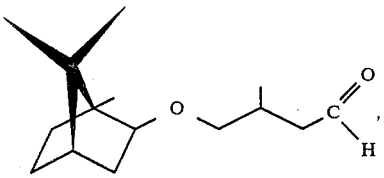

it is to be understood that the instant invention also covers the use of the individual "cis" and "trans" and steroisomers of such compounds, for example, the compound having the structure:

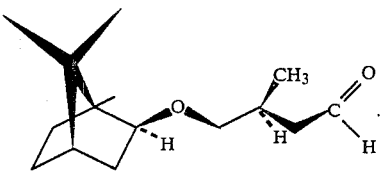

PATENTS INCORPORATED HEREIN BY REFERENCE

The following patents referred to supra are hereby incorporated herein by reference:
U.S. Pat. No. 3,632,396
U.S. Pat. No. 3,948,818
Canadian Pat. No. 1,007,948.

What is claimed is:

1. An ether aldehyde compound defined according to a structure selected from the group consisting of:

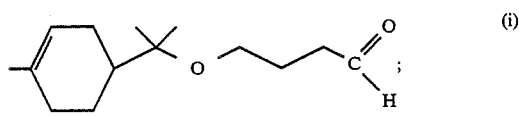

(i)

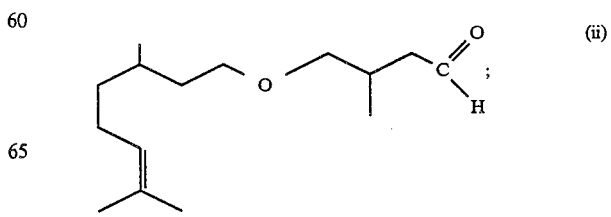

(ii)

-continued

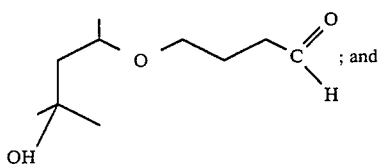; and

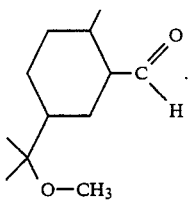

2. A product produced according to the process of reacting a mixture of carbon monoxide and hydrogen with an ether selected from the group consisting of ethers defined according to the structures:

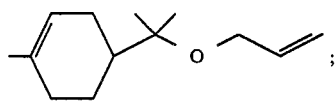;

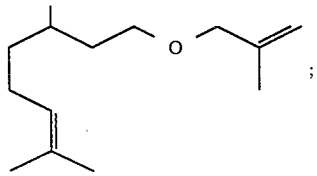;

-continued

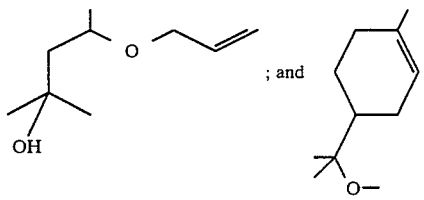; and in the presence of an oxo reaction catalyst whereby a product is produced containing a major proportion of a compound selected from the group consisting of:

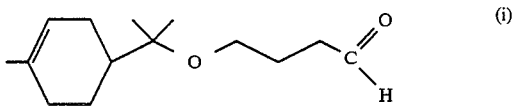

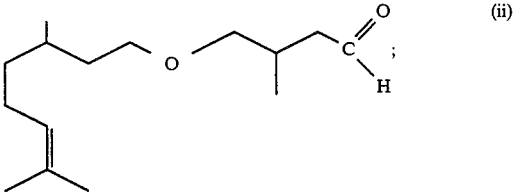;

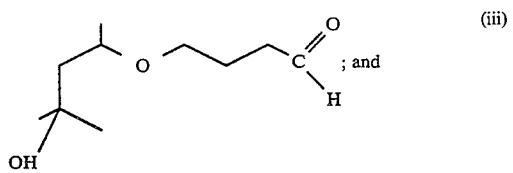; and

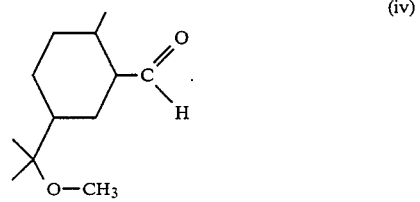

* * * * *